United States Patent
Hildebrandt et al.

(10) Patent No.: US 6,786,081 B1
(45) Date of Patent: Sep. 7, 2004

(54) DIRECT AND/OR OPPOSING FLOWPATH REFRIGERATION

(75) Inventors: Marc J. Hildebrandt, Midland, MI (US); Theodore W. Selby, Midland, MI (US); Richard H. Hall, Midland, MI (US)

(73) Assignee: King Refrigeration, Inc., Freeland, MI (US)

( * ) Notice: Subject to any disclaimer, the term of this patent is extended or adjusted under 35 U.S.C. 154(b) by 0 days.

(21) Appl. No.: 10/077,236

(22) Filed: Feb. 15, 2002

Related U.S. Application Data

(60) Provisional application No. 60/269,372, filed on Feb. 16, 2001, and provisional application No. 60/310,768, filed on Aug. 8, 2001.

(51) Int. Cl.[7] ............................................... G01N 11/14
(52) U.S. Cl. .................... 73/54.43; 73/54.01; 73/54.28; 73/54.35; 73/54.38
(58) Field of Search .............................. 73/54.01, 54.23, 73/54.28, 54.35, 54.37, 54.38, 54.39, 54.43

(56) References Cited

U.S. PATENT DOCUMENTS

| | | | | |
|---|---|---|---|---|
| 4,472,963 A | * | 9/1984 | Gyer et al. ................. | 73/54.34 |
| 5,852,230 A | | 12/1998 | Selby et al. ............... | 73/54.35 |
| 5,877,410 A | * | 3/1999 | Duke ......................... | 73/54.28 |

OTHER PUBLICATIONS

Hildebrandt et al., U.S. provisional 60/269,372 (Feb. 16, 2002).
Hildebrandt et al., U.S. provisional 60/310,768 (Aug. 8, 2002).
ASTM D 4684–98 (1998).
Cannon Instrument Co., Cannon CMRV–4200 Mini–Rotary Viscometer; Mini–Rotary Viscometer Accessories; Mini–Rotary Viscometer CMRV–4300—catalog pp. 47–49.
Reese, K.M., Chemical & Engineering News, Newscripts, Odd device may be the work of Maxwell's demon, Mar. 11, 1996, p. 7.

* cited by examiner

Primary Examiner—Daniel S. Larkin
(74) Attorney, Agent, or Firm—Christopher John Rudy

(57) ABSTRACT

Device for direct refrigeration has heat-conductable solid member with refrigerant passageway coursing through or about; and at least one test sample well in or in proximity to it, at least one solid, heat-generating member affixed or in proximity to it; and/or optional component(s) and/or feature(s). Heat-conductable solid member may have opposing refrigerant flowpaths containing conventional cooling material(s), for example, air, liquid methanol or ethylene glycol, but preferably, refrigerant for direct refrigeration. The member may be, for example, a block of copper and/or other material with a high heat-conductance, with one or more test sample well(s) for insertion of test sample cell(s) for low-temperature rotary viscometric yield stress testing of engine oils, or other testing. Heating may be employed. Dynamic temperature control can be facilitated by temperature sensor and/or controller system, with sensor(s) and/or heating element(s) strategically placed in or on the block. The device may be augmented or conjoined with or to a solid block thermoelectric cooling/heating contrivance which operates by the Peltier effect. Radially endowed correspondent cell pin and rotor bottom cup arrangement can for practical purposes provide nearly friction free action, essentially unencumbered by water/ice interference. Dry gas blanket delivery system and rotor key arrangements are provided as well.

33 Claims, 36 Drawing Sheets

MATCH I.D. TO TEST BLOCK FINISH BORE -0/+0.005

DRILL 0.201 DIA. THRU AND TAP TO 1/4-20 (FULLY THREADED)

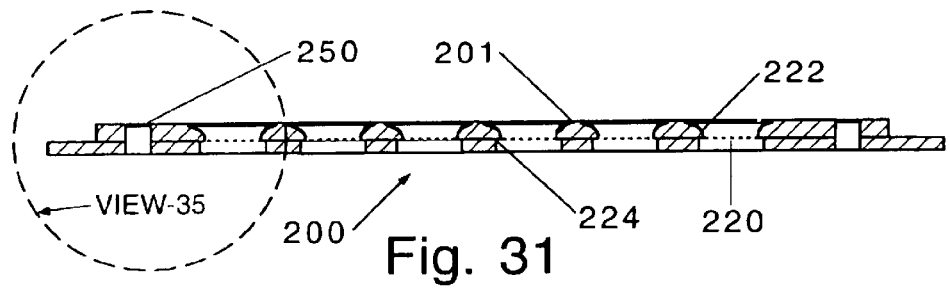
Fig. 31
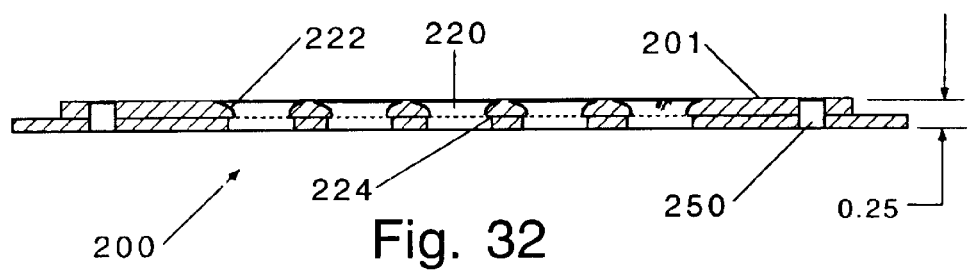
Fig. 32
DRILL 5/32" HOLE
0.10 DEEP FROM
BACK, TYP. 2 PLACES
1/16" GROOVE, 0.110 DEEP
TYPICAL 11 PLACES AS
SHOWN.
1/16" GROOVE, 0.150 DEEP
GROOVE SHOULD CONNECT
5/32" HOLES TO ALL 1/16"
GROOVES 0.110 DEEP
Fig. 33
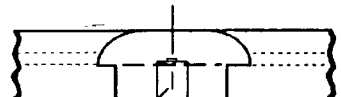
Fig. 34
1/16", 45° CHAMFER
TYPICAL 11 PLACES.
0.256" DIA. THRU
TYPICAL 4 PLACES
MATCH I.D. TO TEST BLOCK
FINISH BORE (-0/+.005). TYP. 11 PLACES
MATCH SHOULDER I.D. TO SLEEVE O.D.
SLIP FIT TYP. 11 PLACES (-0/+.005)
Fig. 35

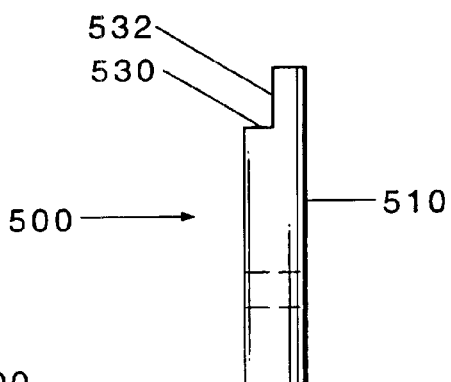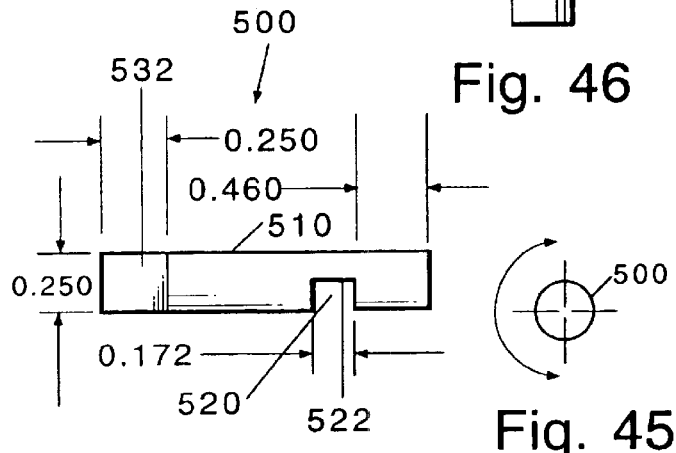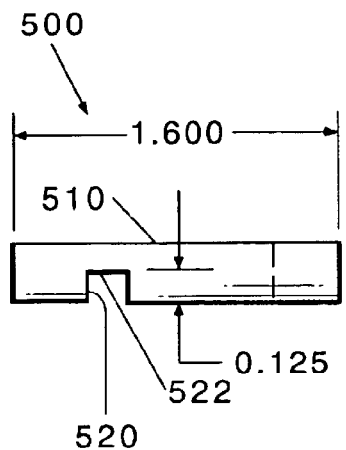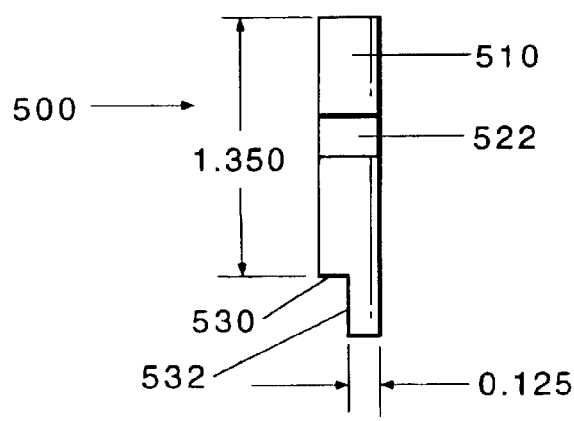

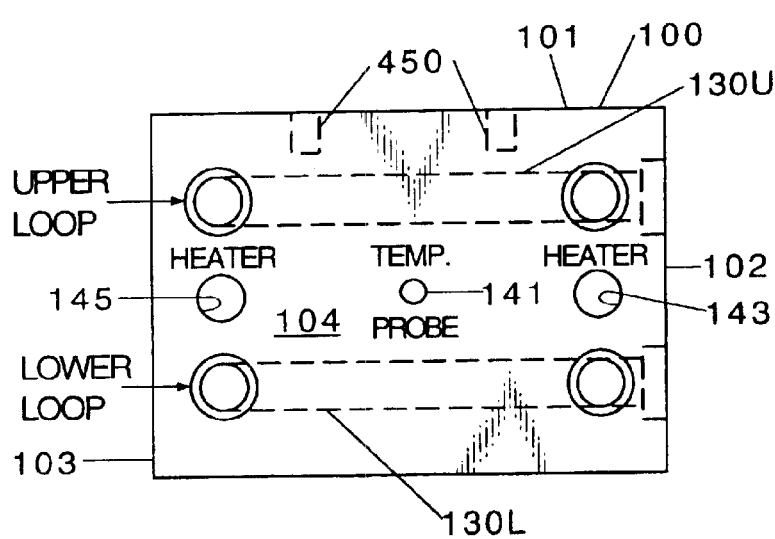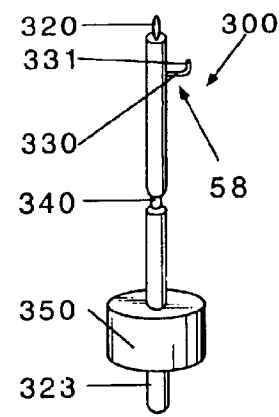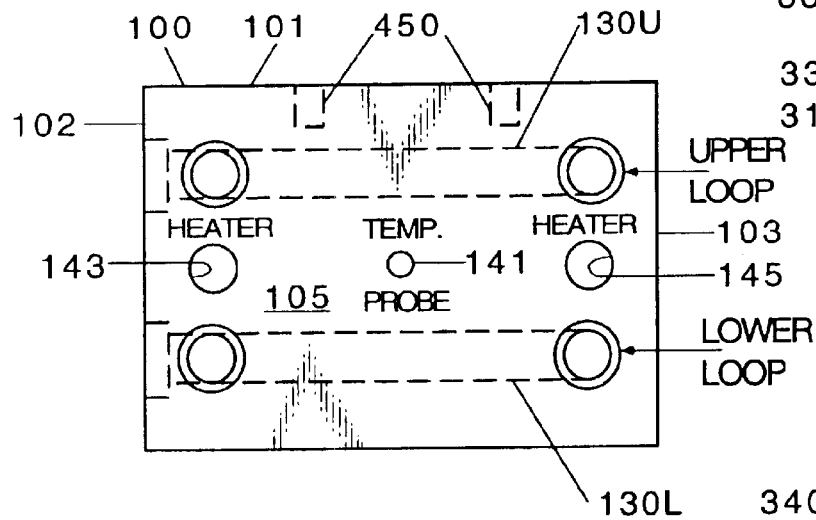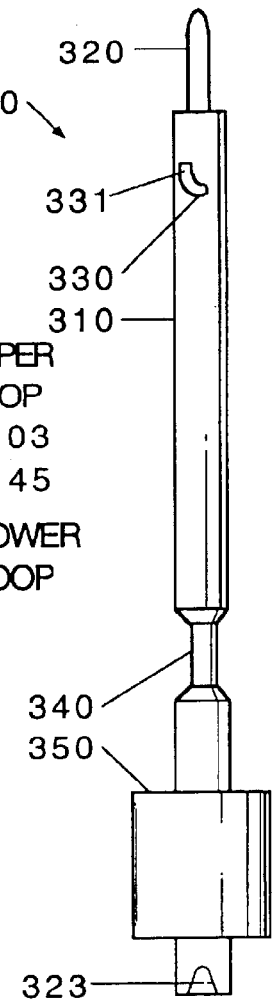
Fig. 55
Fig. 57
Fig. 56
Fig. 58

TYPICAL 11 PLACES

620
INSTRUMENTATION
AND DISPLAYS

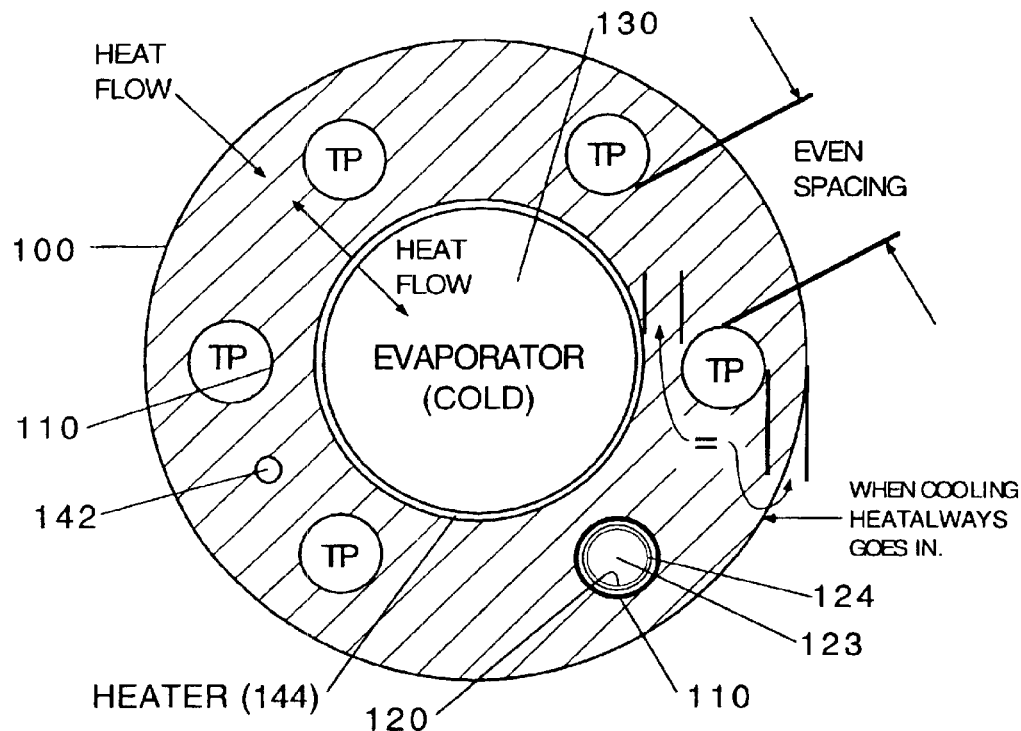
Fig. 80
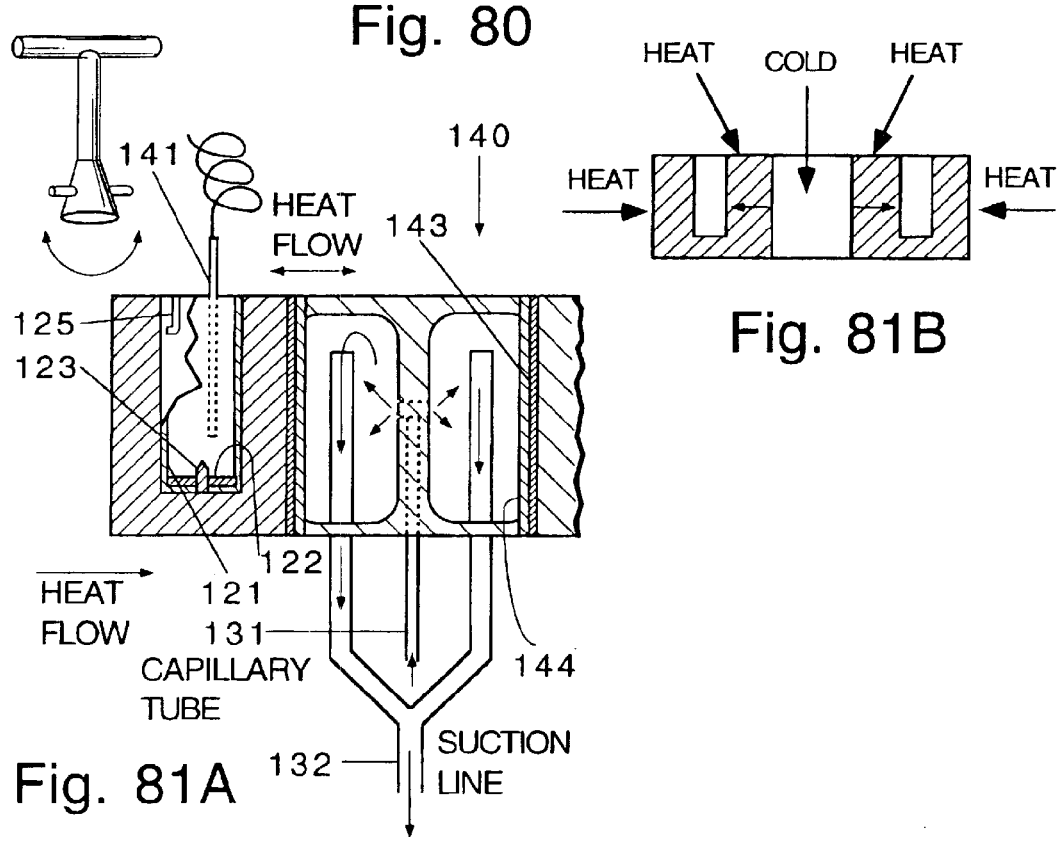
Fig. 81A
Fig. 81B

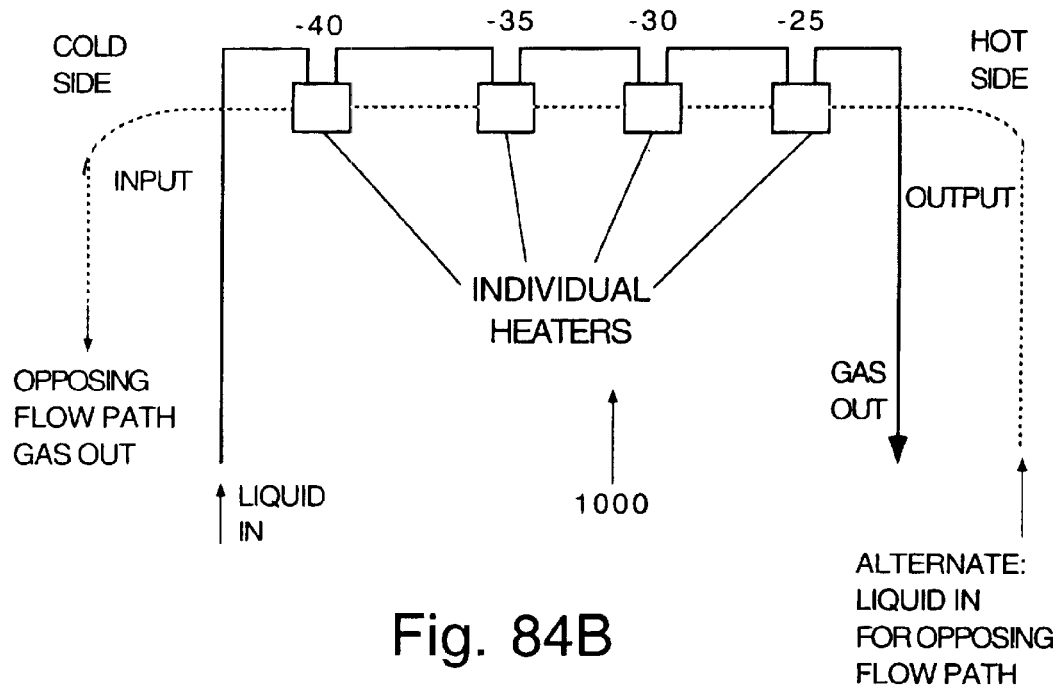
Fig. 84B
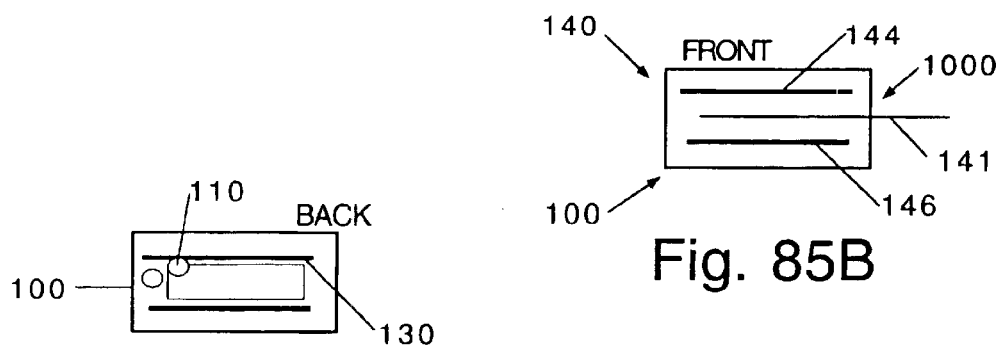
Fig. 85A
Fig. 85B
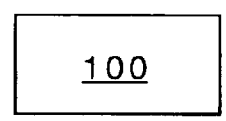
Fig. 85C

US 6,786,081 B1

DIRECT AND/OR OPPOSING FLOWPATH REFRIGERATION

CROSS-REFERENCE CLAIMS OF DOMESTIC PRIORITY

This claims benefit under Section 119(e) of Title 35, United States Code, of U.S. provisional patent application Nos. 60/269,372 filed on Feb. 16, 2001 A.D., and 60/310,768 filed on Aug. 8, 2001 A.D. The complete specifications of both of those applications are incorporated herein by reference.

FIELD AND PURVIEW OF THE INVENTION

The present invention concerns a device for direct refrigeration of a component of a system or the entire system by which a cooling intermediary, such as methanol or other liquid can be avoided, and, in another embodiment, a refrigeration device, which, in general, employs opposing refrigeration flowpaths in a cooling block. Heating may be conducted. Such can be employed in conjunction with a solid block, thermoelectric device to enhance heat transfer cooling, and/or temperature control with the Peltier effect. The invention is useful especially in direct cooling and/or temperature control of solid components, which, in one embodiment, can be part of an instrumental system for low temperature viscometric testing of engine oils and so forth, say, to determine yield stress and apparent viscosity of the oils; and, in other embodiments, can be for various other applications as, for instance, to cool various heat-emitting electronic components, centrifuges, industrial machinery, and so forth.

BACKGROUND TO THE INVENTION

The performance of engine oils and other lubricants at low temperatures has been of increasing concern, and various art has been developed in order to ascertain, in advance, properties of the oils which would be determinative of the likely success or failure of the oil under low temperature operating conditions, especially in start up and cold temperature operation of motor vehicle internal combustion engines. In the testing of engine oils at low temperatures, it is critical for performance of the test that the test oil be maintained at a particular temperature and/or be controlled to have a certain rate of increase or decrease in temperature. For example, ASTM D-4684-98 covers the determination of yield stress and apparent viscosity of engine oils after cooling at controlled rates over a period exceeding forty-five hours to a final test temperature of between minus fifteen and minus thirty-five degrees Celsius. That standard test method specifies circulation of liquid coolant, for example, methanol, to cool the test block and, in turn, the test cells.

In addressing such requirements, certain devices have been provided. For example, the standard instrument in its field for the ASTM D-4684 test method is the Mini-Rotary Viscometer (MRV) from Cannon Instrument Co., State College, Pa. Developed in the 1970s, the MRV in general provides for a rough viscometric method to obtain data under low temperature conditions at, however, only one temperature at a time. The MRV has an aluminum block, which temperature is controlled by a refrigerated methanol bath that requires a circulating system to pump the coolant from from the refrigeration device to the block, and back again to the bath to cool the block. A temperature-controller in the aluminum block is employed to attempt to hold the temperature at the programmed set temperature. Among drawbacks further may be mentioned a lack of precision and accuracy, as cooling of the aluminum block by the cooling fluid is carried out along a flow path through the block. Accordingly, the MRV block is cooler at its cooling fluid entry end than at its exit end, notably because of temperature gain from the environment of the room; this effect is exaggerated at colder test temperatures. Thus, in general, the temperature so necessary to development of accurate data for sooted and/or highly oxidized oils is not held well by today's standards, with, for example, a five-degree Celsius temperature differential from end to end of the instrument often found. And, water in MRV test cells can be problematical, especially at low temperatures, with "frosting" an impediment, and in consideration of its test cell design with a "well" raised above the bottom of the cell. At the lower temperatures, the MRV weaknesses noticeably show. Also, the use of methanol, a hazardous material, can be problematical from standpoints of laboratory practice and personnel safety.

An improvement is the device to test pumpability of oils at low temperature of Selby et al., U.S. Pat. No. 5,852,230. With the device of Selby et al., all stators that are filled with test fluid can be positioned in a carousel arrangement, which can be immersed into a temperature control bath, and held at the same temperature through a spaced-apart stator array and the mobility of the temperature control bath fluid, for example, methanol. As a result, test accuracy and precision are notably advanced. As well, among other things, with that device, a greater number of test cells can be tested simultaneously. However, the device has need of an intermediary bath, which again is typically methanol.

Moreover, many devices or components in devices which generate their own heat can be damaged or have inferior performance through excessive heat. For example, CPU chips require cooling, which is provided by relatively inefficient air fans, to remain operable; and known superconducters depend upon cold temperatures to be operable.

It would be desirable to improve upon the foregoing.

SUMMARY WITH INTRODUCTORY DETAIL OF THE INVENTION

In a basic, and desirable aspect, the present invention provides a device for direct refrigeration comprising a heat-conductable solid member having a refrigerant passageway coursing through or about, and at least one of the following:

at least one test sample well therein or in proximity thereto;

at least one solid, heat-generating member affixed or in proximity thereto; and optionally, additional component(s) and/or feature(s).

In another aspect, a heat-conductable solid member may have opposing refrigerant flowpaths coursing therethrough, said flowpaths containing conventional cooling material(s), for example, cooled air, or liquid methanol or ethylene glycol, but preferably, a refrigerant for direct refrigeration. The member may be, for example, a block of copper and/or other material with a high heat-conductance, with one or a plurality of test sample well(s) for insertion of viscometric test sample cell(s) for viscometric or other type testing. Heating may be employed in conjunction therewith. Accordingly, the device can be adapted for use in a test to determine yield stress and apparent viscosity of engine oils at low temperature by providing a rotor, and optionally, but preferably, a test cell sleeve, for insertion in a respective test sample well. Dynamic temperature control can be facilitated by a temperature sensor and/or controller system, with sensor(s) and/or heating element(s) strategically placed in or on the block. The device may be augmented or conjoined with or to a solid block thermoelectric cooling/heating contrivance which operates by the Peltier effect. Beneficially, the block is made of a generally inert material, for instance, a metal, with a high heat conductance, for example, copper or gold. A special, radially endowed correspondent cell pin and rotor bottom cup arrangement can for practical purposes provide nearly friction free action, essentially unencumbered by water/ice interference, and a unique dry gas blanket delivery system can be provided. As well, unique rotor key arrangements can be provided. Other aspects include methods of use of the device.

The device is useful in cooling, temperature control, and, in certain particular embodiments, fluid characterization testing.

Significantly, by the invention, problems in the art are ameliorated, if not eliminated or overcome. Not the least of these is the elimination of intermediating cooling liquid, such as methanol, if so desired. Thus, the device can be made to be more compact, efficient to make, and very easy and efficient to use including in set up, running, controlling, and cleaning, and free from the hazards which attend the use of methanol. Air or liquid cooling of electronic to include computer or mechanical parts is also improved by the direct cooling. As if that were not enough, exacting, nearly pinpoint standards of temperature control with the device are achieved if not set outright, and, with a dynamic temperature regulating system, the device can be used in obtaining data through accurately and precisely scanning a range of temperature rather than being limited to one temperature per test. Such high standards of temperature control with the device can occur through employment of the opposing refrigerant flowpath system. Embodied for employment in a test to determine yield stress and apparent viscosity of engine oils at low temperature, operation of and data collection of plural samples with the device are greatly improved by a radially arranged sample well array such as the radially endowed correspondent cell pin and rotor cup system. As well, the unique dry gas blanket delivery system, in addition to the cell pin and rotor cup system, can ameliorate if not eliminate the impediment of "frosting." The unique key arrangements and other features can facilitate greater efficiency in testing as well. Individual cell control can also be achieved by single cell cooling and temperature control. Moreover, the Peltier effect can be put to advantageous use without the need for exotic refrigerants or excessive mechanical refrigeration cascades so that cooling with more standard refrigerants can be lowered forty degrees C. With such solid block thermoelectric cooling/heating contrivances, in general, a range of eighty degrees C can be modulated by and/or used as a modulator for the cooling provided by the direct refrigeration device. Also, various heat-emitting electronic components, centrifuges and machinery can be cooled directly. For example, superconductors or superconductive devices can be cooled directly as well as can be computer component, such as computer processing unit (CPU) chips and mainframe boards; cryogenic devices; other types of heat-emitting electronic components; centrifuges; pumps; metal-cutting and injection-molding machinery; clamps; bearings; and so forth. In fine, the invention may be employed nearly anywhere a component or system, especially that which includes a solid member, which may generate its own heat, needs cooling and/or temperature control.

Numerous further advantages attend the invention.

THE INVENTION ILLUSTRATED WITH RESPECT TO DRAWINGS

The drawings form part of the specification hereof. With respect to the drawings, which are not necessarily drawn to scale and in which, if dimensions are listed, they are listed in inches (") unless otherwise noted (with dimensions typically taken to places, such as X.XXX to +/−0.002; X.XX to +/−0.010; fractions to +/−1/32; angles to +/−1-degree) and are to be considered exemplary and may be considered approximate or to be varied from in the practice of the invention, the following is briefly noted:

Abbreviations may be employed. A table of abbreviations found, especially with the drawings, and their meanings follows:
CaCl2 Calcium chloride.
DIA. Diameter.
E Energy/refrigeration.
E.G. Exempli gratia (for sake of an example).
ETC. Et cetera (and others; and so on: and so forth).
H Heat.
HP Horsepower.
I.D. Inside diameter.
O.D. Outside diameter.
PSI Pressure or pounds per square inch.
R Radius.
RAD. Radius.
RTD Resistance temperature detector.
TEMP. Temperature.
THRU Through.
TP Test port.
TYP. Typical/typically.
V Valve.
W Watt.
W/ With.

Also, symbols may be employed. A table of the symbols found, especially in the drawings, and their meanings follows:
∝ Angle.
° Degree.
φ Diameter.
" Inch.
Number FIG. 1 is a front view of an embodiment of a device for low temperature viscometric testing of the invention, including components of a heat-conductable solid member (block), which is in the form of a rectangular solid; plate; rotor; one-piece key; and dynamic temperature control system. The device has a one-way refrigerant flowpath in its block. Such an embodiment is especially useful in a test to determine yield stress and apparent viscosity of engine oils at low temperature (TP-1).

FIG. 2 is a rear view of the device of FIG. 1.
FIG. 3 is a left side view of the device of FIG. 1.
FIG. 4 is a right side view of the device of FIG. 1.
FIG. 5 is a top, perspective view of the intermediate top plate insert from the device of FIG. 1.
FIG. 6 is an exploded view, in perspective, of the bottom of the insert of FIG. 5 showing its dry gas delivery (distribution) channels, and of a sealing gasket having adhesive for securing to the insert to enclose the delivery channels.
FIG. 7 is a side view of a stop key of the device of FIG. 1.
FIG. 8 is a side view of a standoff of the device of FIG. 1.
FIG. 9 is a perspective plan view of an insertable test cell employed with the rotor of FIG. 9 in the device of FIG. 1.
FIG. 10 is a side view of a T-arm type rotor employed in the device depicted in FIG. 1.
FIG. 11 is a plan view of a device for low temperature viscometric testing including a device such as of FIG. 1, with refrigerant supply and electric/electronic dynamic temperature control sources.

FIG. 31 is a side, sectional view of the intermediate top plate insert of FIG. 30, taken along 31—31 in FIG. 30.

FIG. 32 is a side, sectional view of the intermediate top plate insert of FIG. 30, taken along 32—32 in FIG. 30.

FIG. 33 is a top plan view, in detail, of part of the intermediate top plate insert of FIG. 30, taken from within the circle 33 in FIG. 30.

FIG. 34 is a side plan, sectional view, in detail, of part of the intermediate top plate insert of FIG. 30, taken along viewing arrow 34 in FIG. 33.

FIG. 35 is a side, sectional view, in detail, of part of the intermediate top plate insert of FIG. 30, taken from within the circle 35 in FIG. 31.

Figure 36:
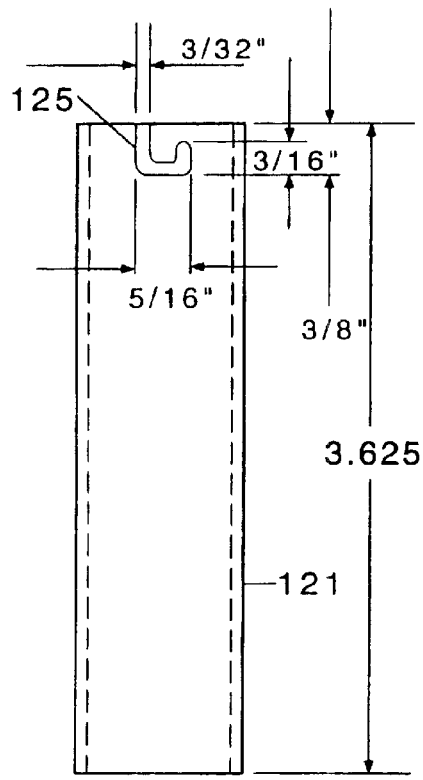
FIG. 36 is a side plan view of a centerless ground, insertable test cell cylinder component having opposing J-slots (rear J-slot omitted for clarity) found within the assembled test cell of FIG. 9, employed within the device of FIG. 1. All sharp edges are broken.
Figure 37:
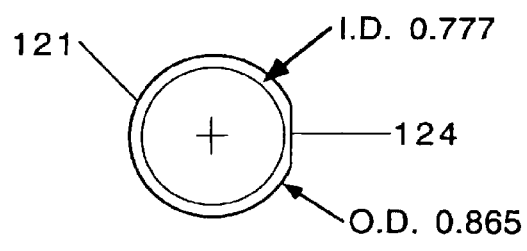

FIG. 37 is a top view of the test cell cylinder of FIG. 36. The flat side is ground (flat) 0.02" maximum for air relief. This must be done after bottom is installed; the rotor O.D. is adjusted to the cell finish I.D., and the noted cylinder O.D. is a minimum; desired rotor and cell dimensions include a rotor O.D. of 0.669" and a cell I.D. of 0.787" or as noted.

Figure 38:
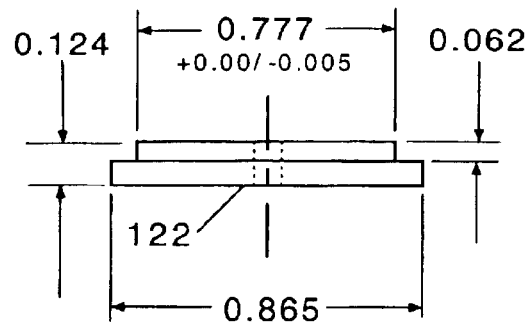

FIG. 38 is a side plan view of a test cell cylinder plug assembled with the cylinder of FIGS. 36 and 37. The plug should fit inside the cell up to a first shoulder; the finish O.D. is matched to the cell finish O.D.; all sharp edges are broken.

Figure 39:
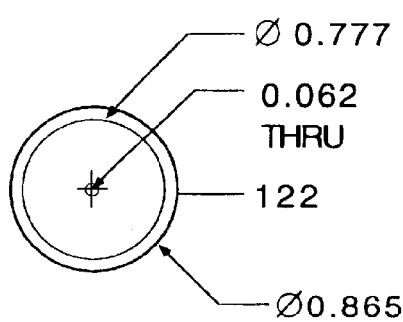

FIG. 39 is a top plan view of the plug of FIG. 38.

Figure 40:

FIG. 40 is a top plan view of a rotor-engaging stator pin assembled with the plug of FIGS. 36 and 37. All sharp edges are broken.

Figure 41:
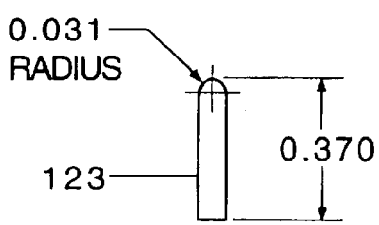

FIG. 41 is a side plan view of the pin of FIG. 40. The pin is silver-soldered into the plug so that the pin is flush with the bottom of the plug; then the plug is silver-soldered into the cell; this must be water-tight.

Figure 1:
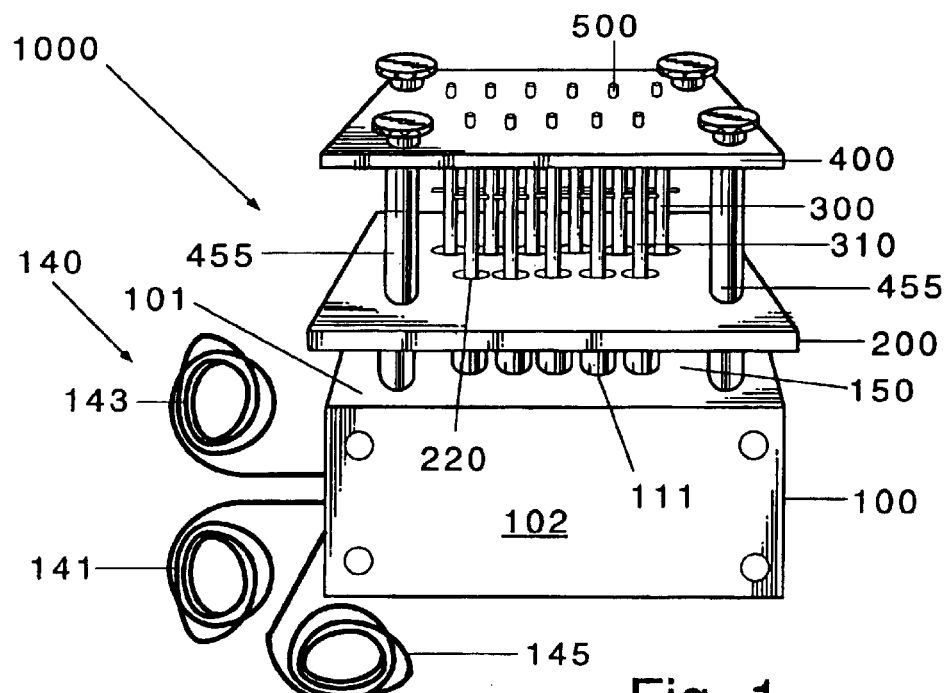
Figure 2:
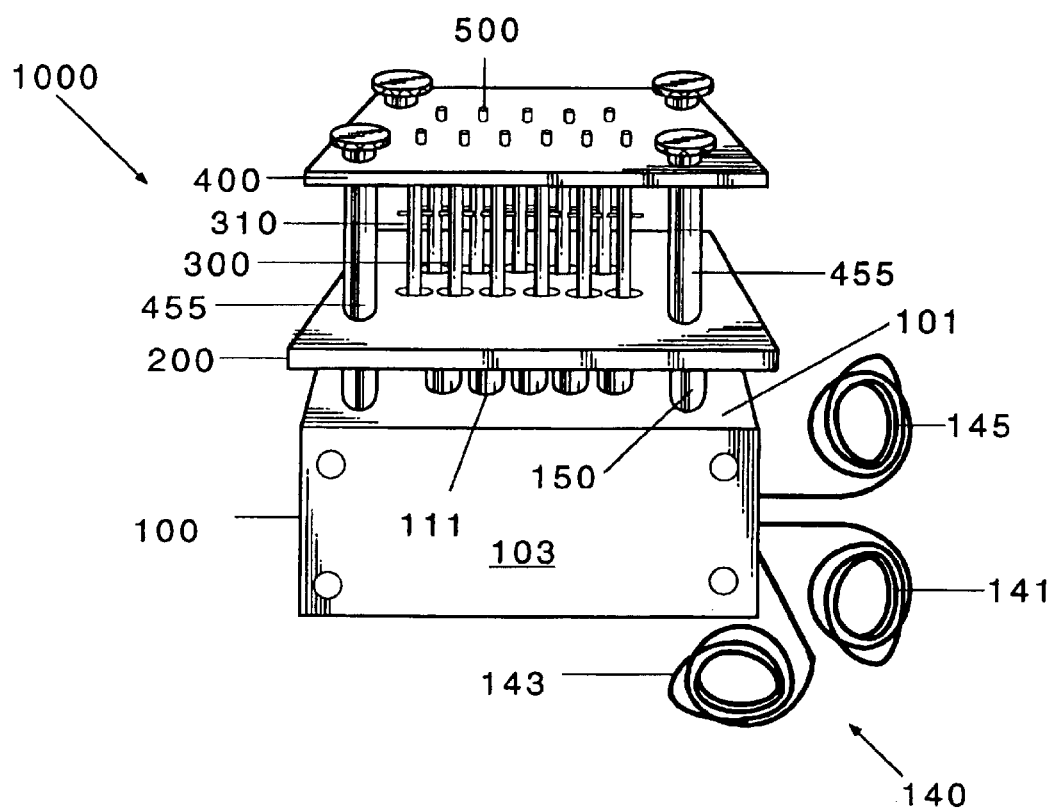
Figure 3:
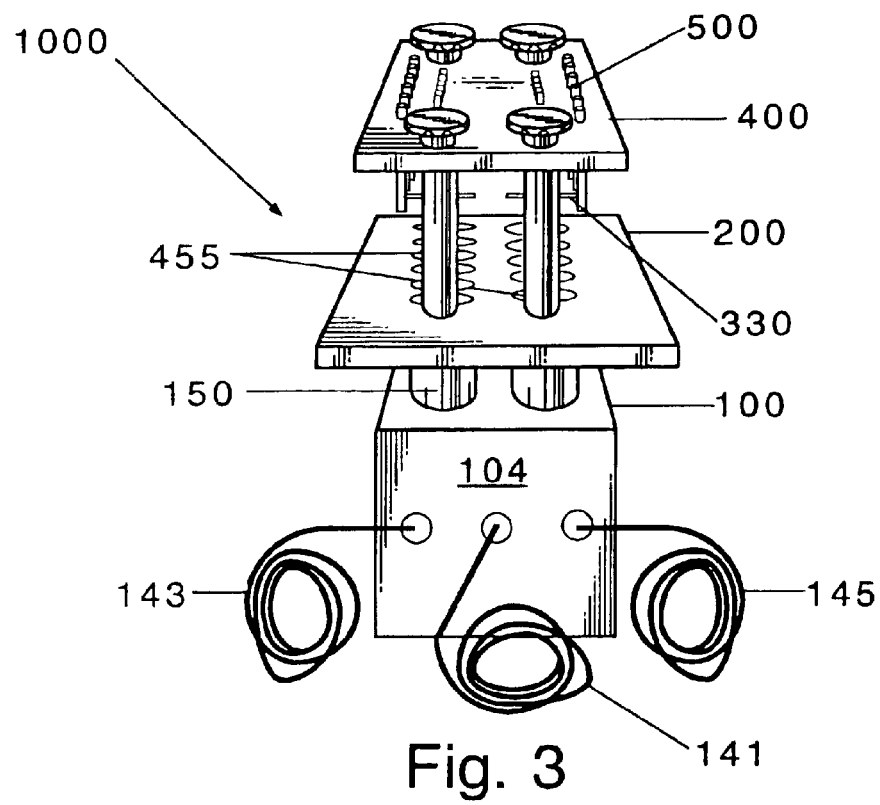
Figure 4:
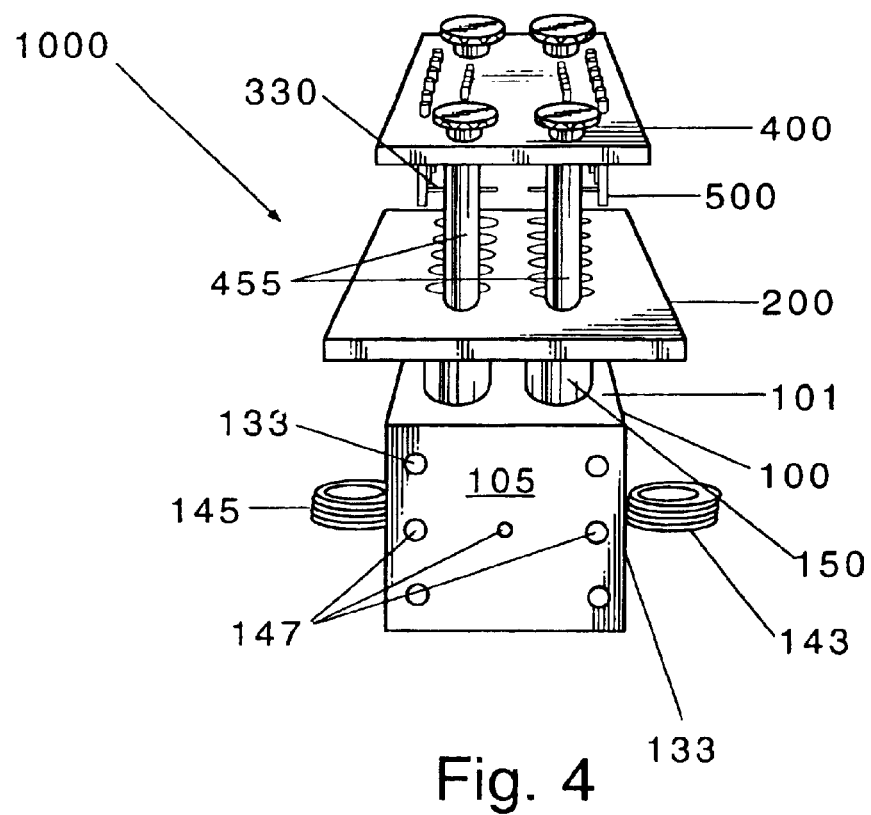
Figure 5:
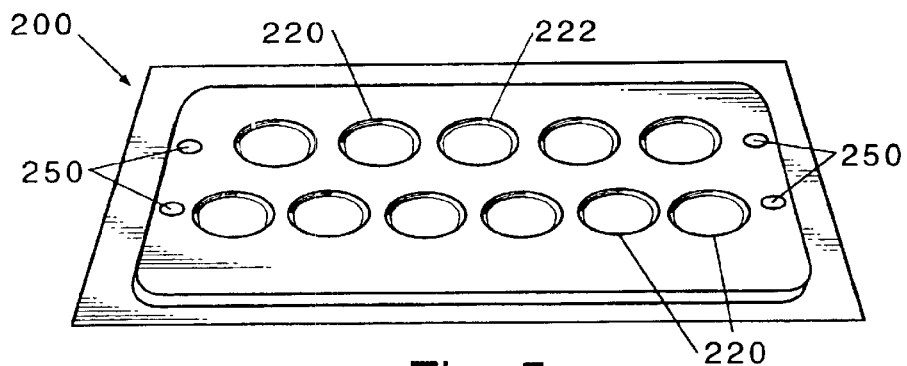
Figure 6:
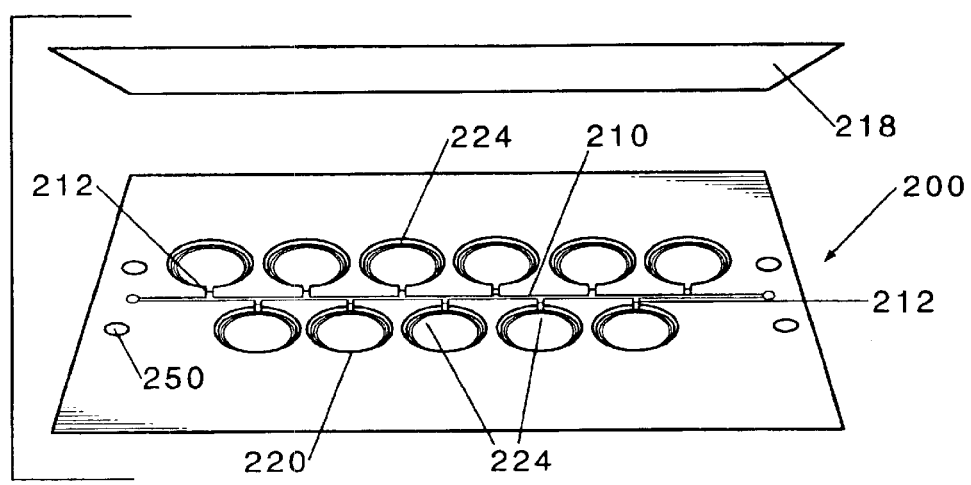
Figure 10:
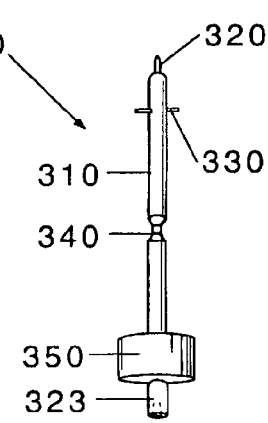
Figure 11:
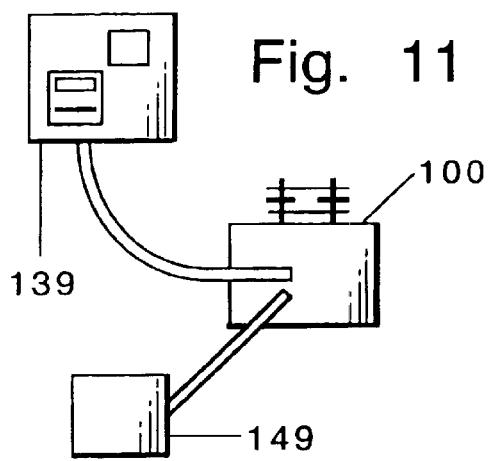
Figure 12A:
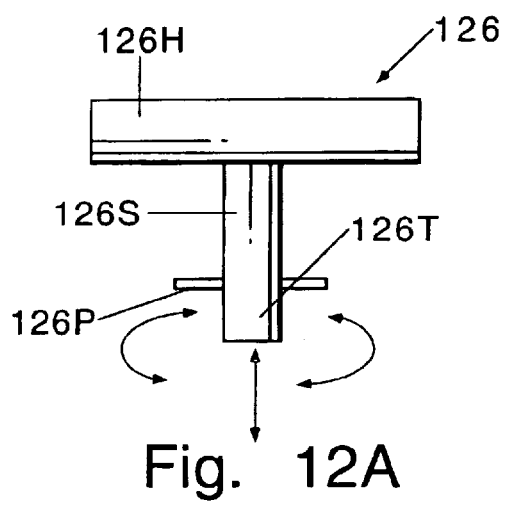
FIGS. 12A, 12B and 12C depict T-tools (12A and 12B, side views; 12C, perspective view) of T-tools to assist in removal of test cell insert sleeves which have J-slots.
Figure 12B:
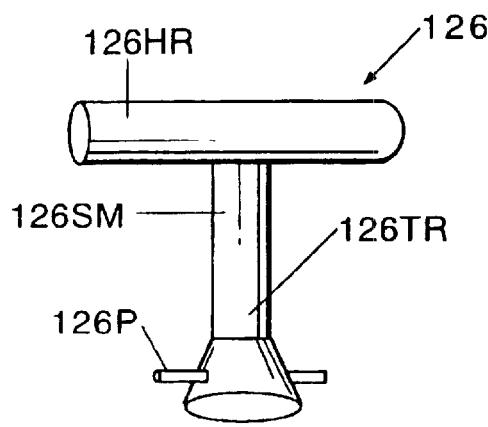
Figure 12C:
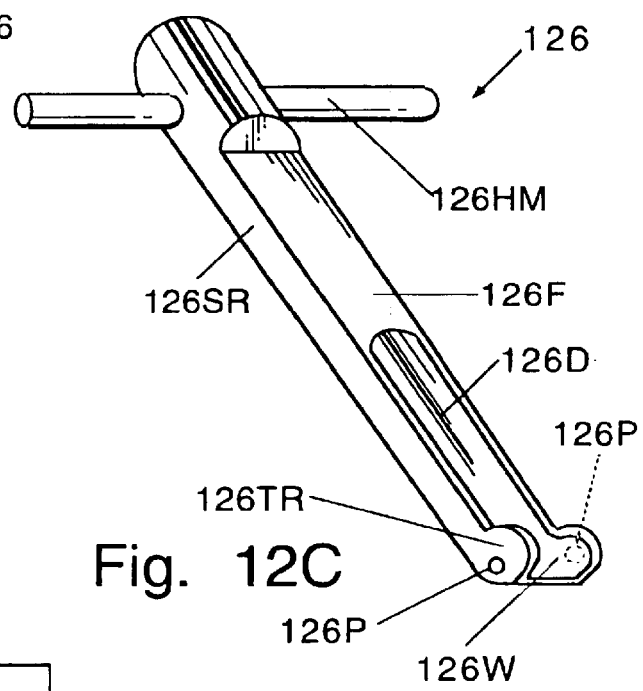
Figure 13:
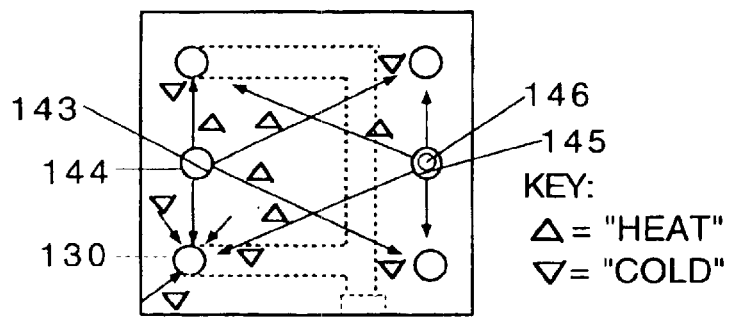
FIG. 13 is a left side view of a block of the invention, for example, made of copper, for employment in the device for low temperature viscometric testing, illustrating heat and cold fluxes (which are both actually heat fluxes) in dynamic temperature control.
Figure 14:
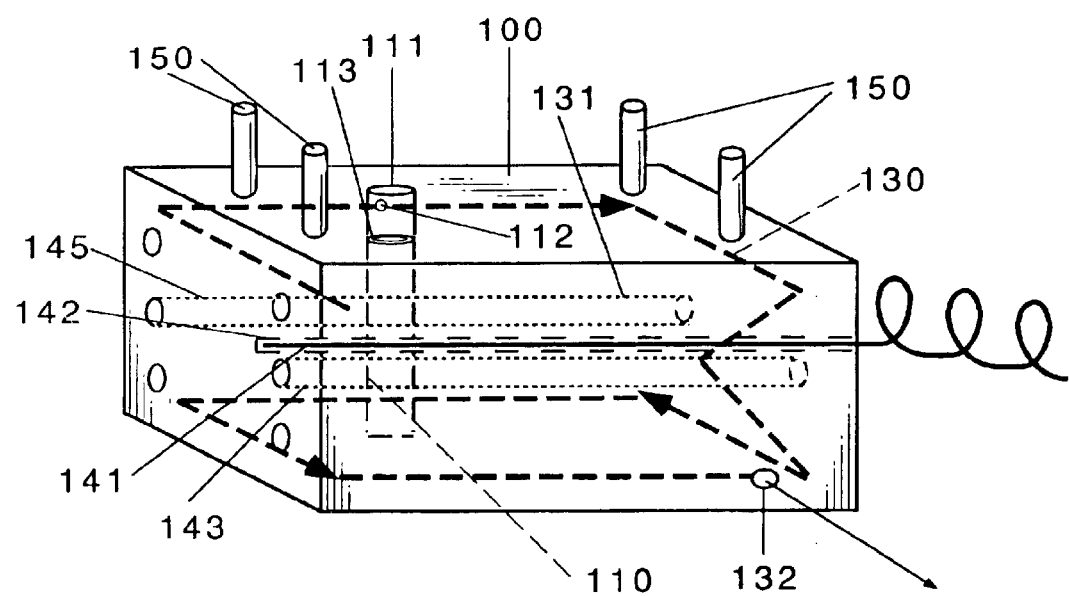
FIG. 14 is a perspective plan view of a device for low temperature viscometric testing of the invention, in a state of partial construction.
Figure 15:
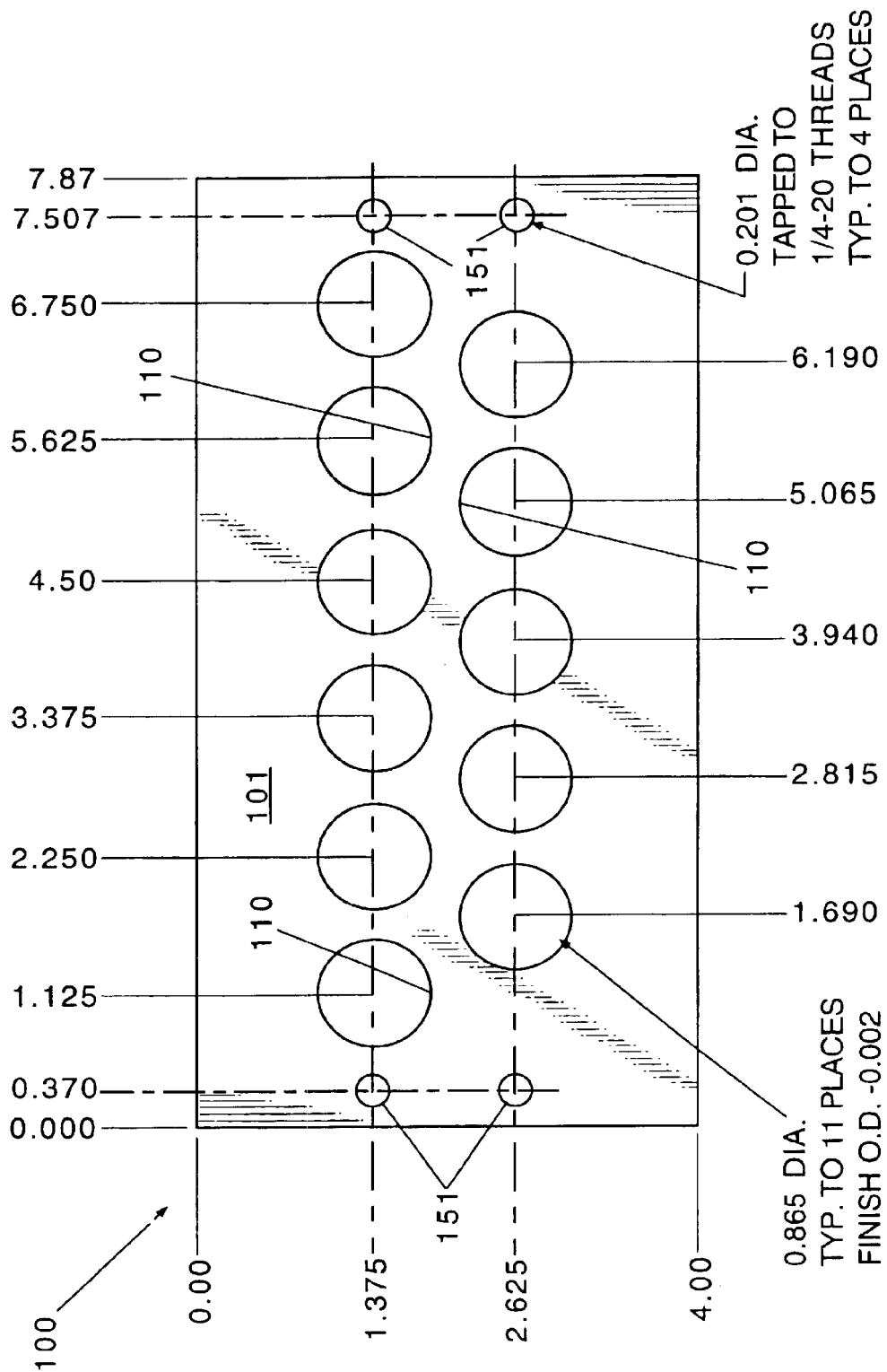
FIG. 15 is a top plan view of the block employed within the device of FIG. 1, with hidden lines omitted for clarity. The finish I.D. of the cell wall is matched to the test cell; surface finish is #62 with all sharp edges broken.
Figure 16:
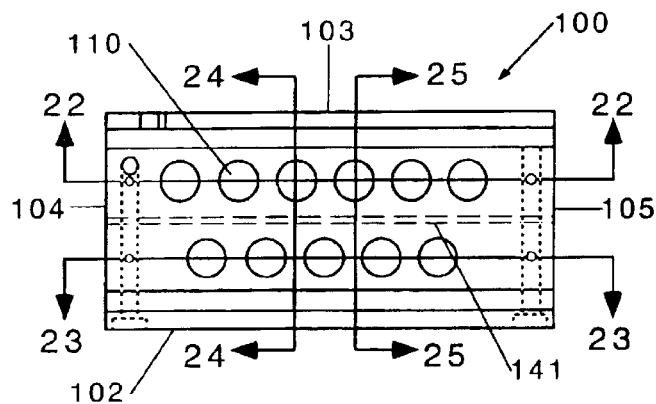
FIG. 16 is a top plan view of the block depicted in FIG. 15.
Figure 17:
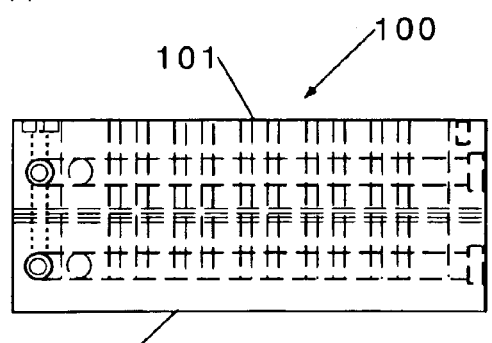
FIG. 17 is a front view of the block depicted in FIG. 15.
Figure 18:
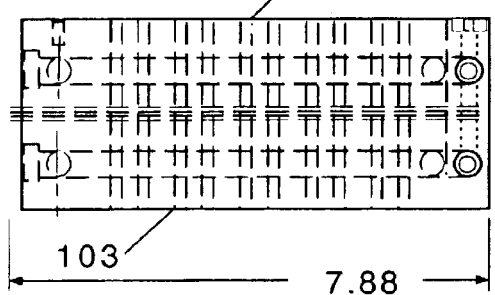
FIG. 18 is a rear view of the block depicted in FIG. 15.
Figure 19:
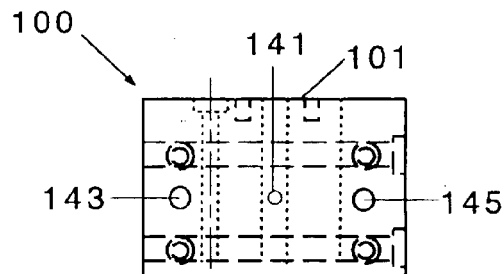
FIG. 19 is a left side view of the block depicted in FIG. 15.
Figure 20:
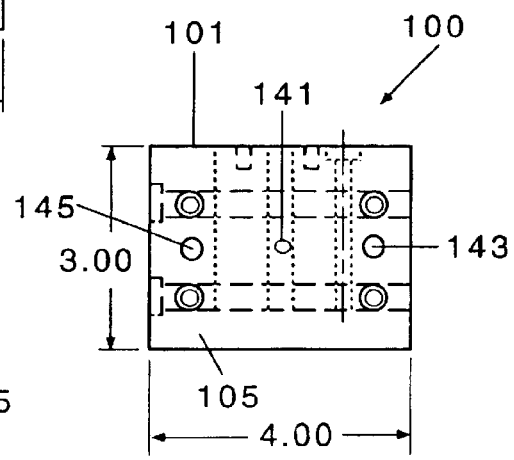
FIG. 20 is a right side view of the block drawn in FIG. 15.
Figure 21:
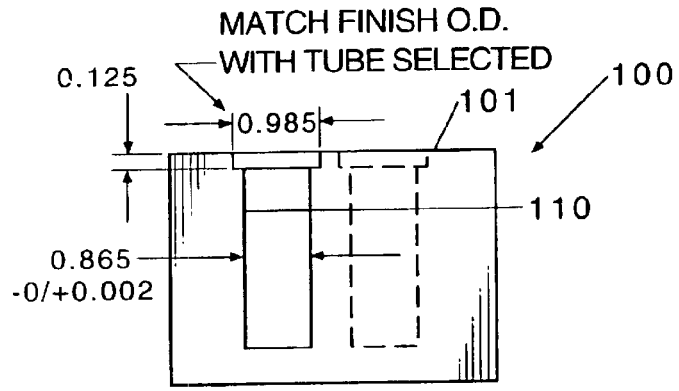
FIG. 21 is a side plan view of the block depicted in FIG. 15, showing detail for test ports (cell wells).
Figure 22:
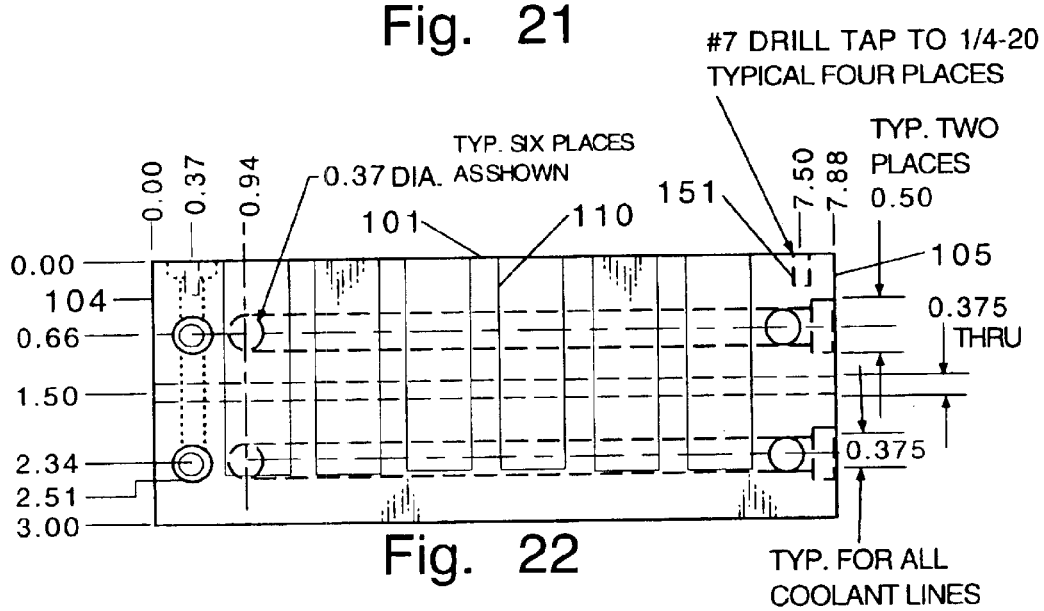
FIG. 22 is a sectional plan view of the block depicted in FIG. 15, taken along 22—22 in FIG. 16.
Figure 23:
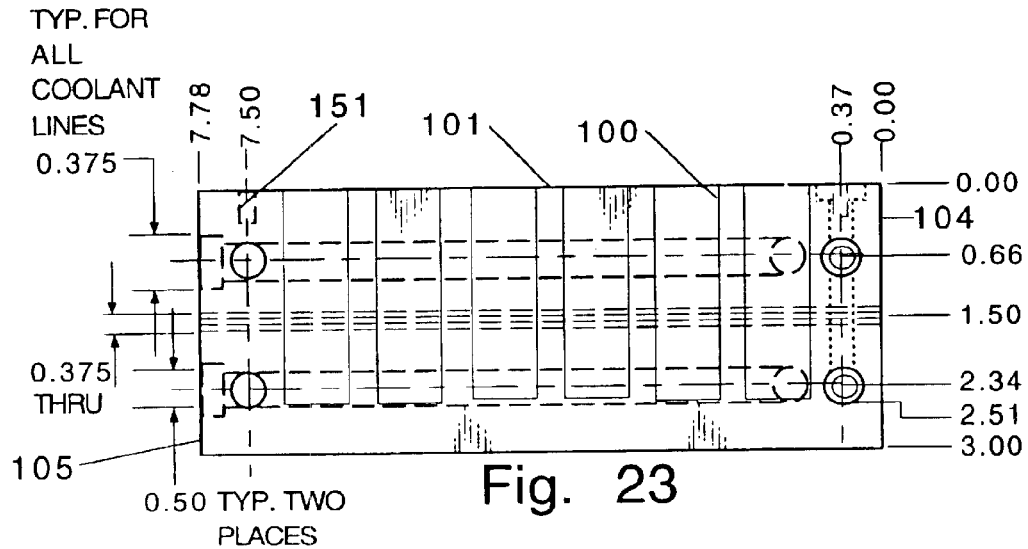
FIG. 23 is a sectional plan view of the block depicted in FIG. 15, taken along 23—23 in FIG. 16.
Figure 24:
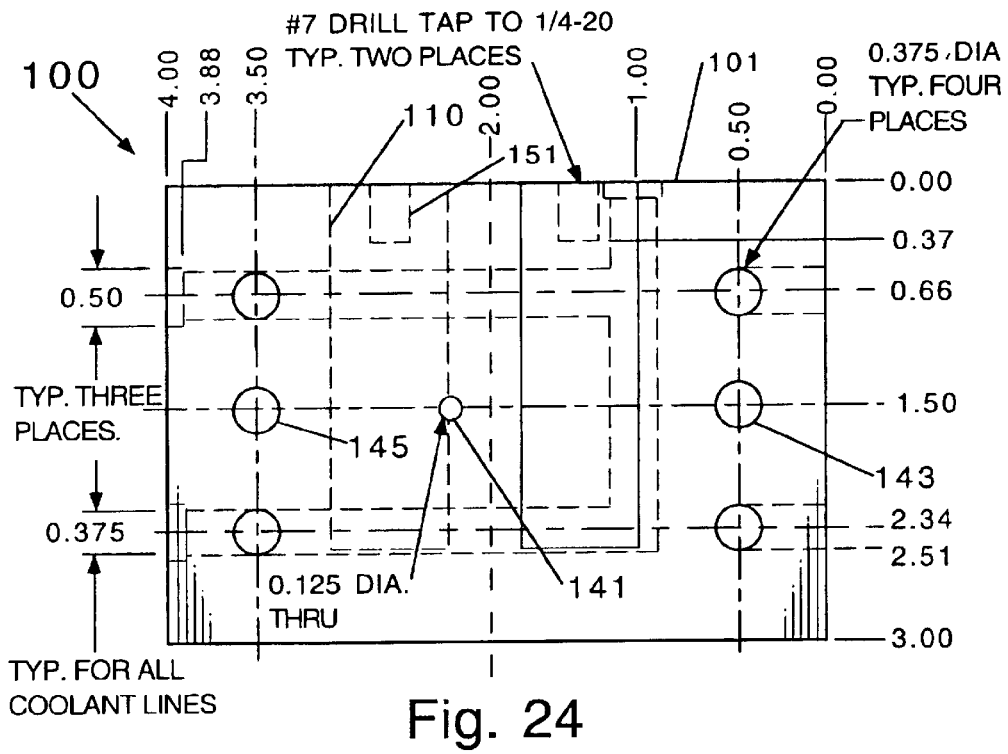
FIG. 24 is a sectional plan view of the block depicted in FIG. 15, taken along 24—24 in FIG. 16.
Figure 25:
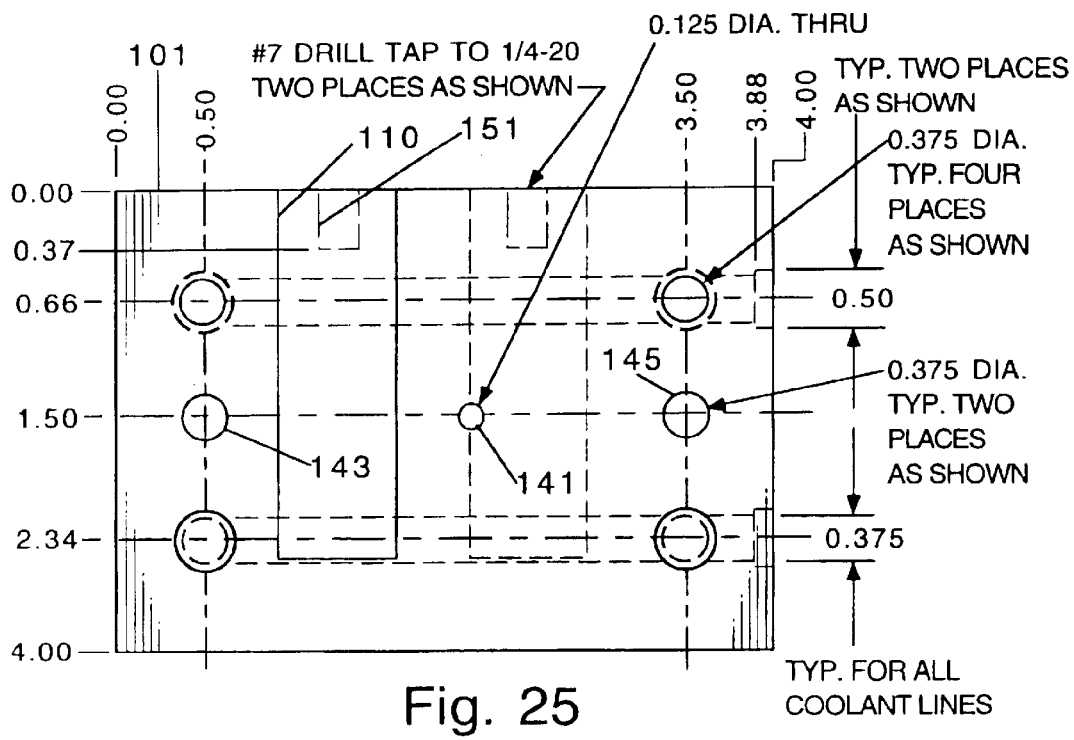
FIG. 25 is a sectional plan view of the block depicted in FIG. 15, taken along 25—25 in FIG. 16.
Figure 26:
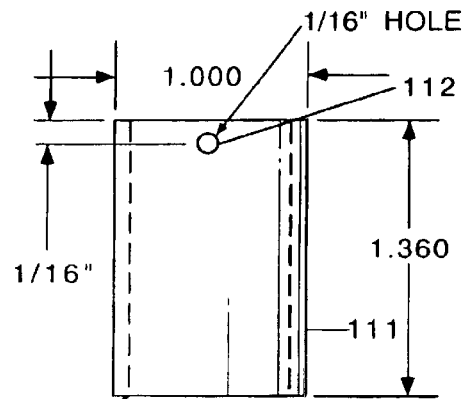
FIG. 26 is a side plan view of a cell well extension (internal sleeve), for example, made of #303/304-stainless steel, in the device of FIG. 1. The test block shoulder I.D. is matched to the sleeve O.D. with a slip fit; only one 1/16" hole is provided, only thru one side; surface finish is #62 with all sharp edges broken.
Figure 27:
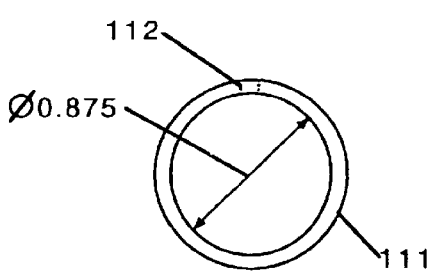
FIG. 27 is a top plan view of the internal sleeve of FIG. 26.
Figure 28:
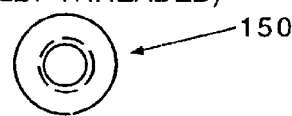
FIG. 28 is a top plan view of an internal standoff, for example, made of DELRIN plastic, in the device of FIG. 1.
Figure 29:
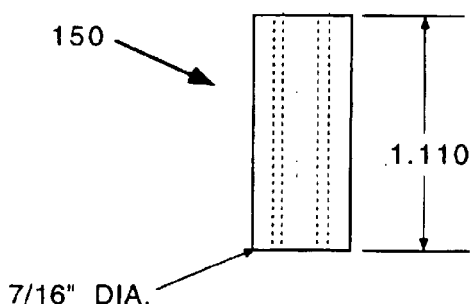
FIG. 29 is a side plan view of the standoff of FIG. 28.
Figure 30:
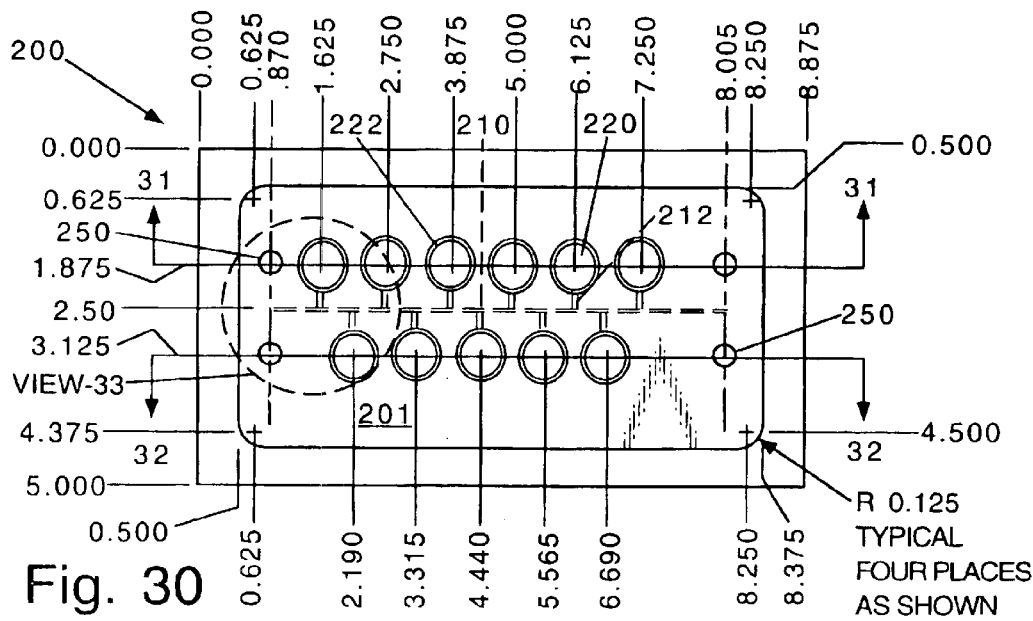
FIG. 30 is a top plan view of the intermediate top plate insert of FIGS. 5 and 6, employed within the device of FIG. 1. Surface finish is #32 with all sharp edges broken.
Figures 42, 43:
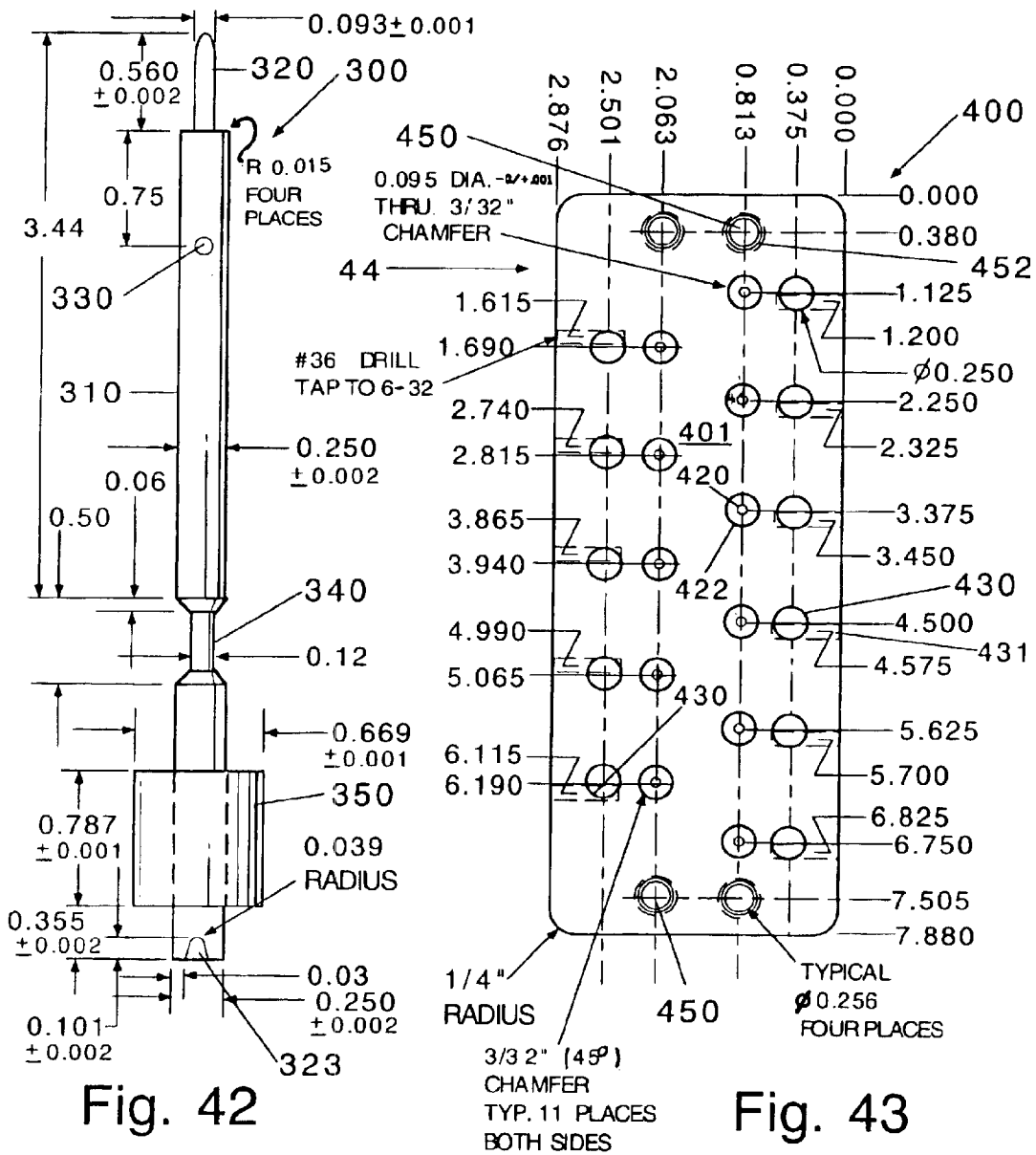

FIG. 42 is a side plan view of the rotor of FIG. 10, employed with the device of FIG. 1. The upper tip is turned down to a 0.0937-inch diameter, and the radius end to 0.046 inch; the drum is press fit th the rotor shaft; all sharp edges are broken.

FIG. 43 is a top plan view of the top plate found within the device of FIG. 1. The chamfered top bearing holes must be burr free; all sharp edges are broken.

Figure 44:
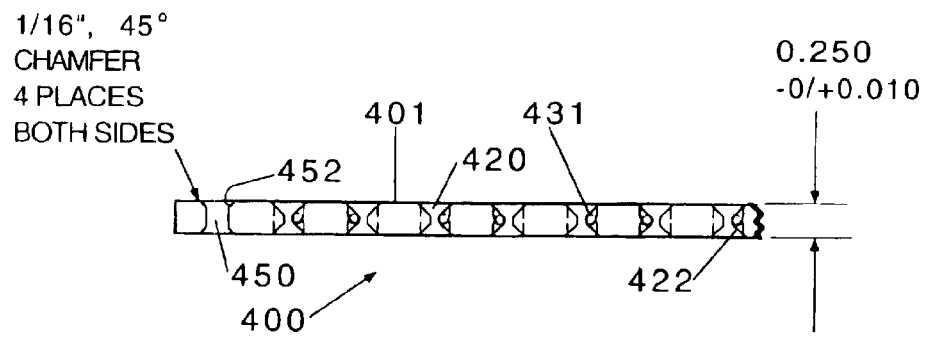

FIG. 44 is a side plan view of the top plate of FIG. 43, taken along viewing arrow 44 in FIG. 43.

Figure 7:
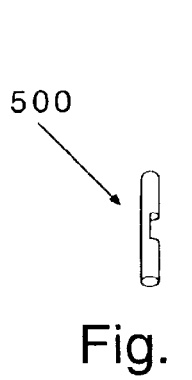
Figure 8:
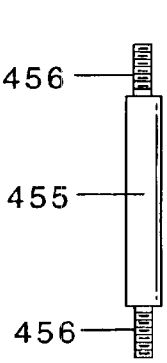
Figure 9:
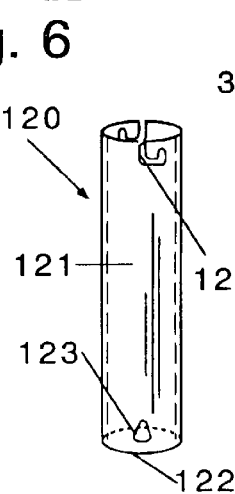

FIGS. 45–49 are plan views of the one-piece stop key depicted in FIG. 7, employed in the device of FIG. 1. Surface finish is #32 with all sharp edges broken.

Figure 50:
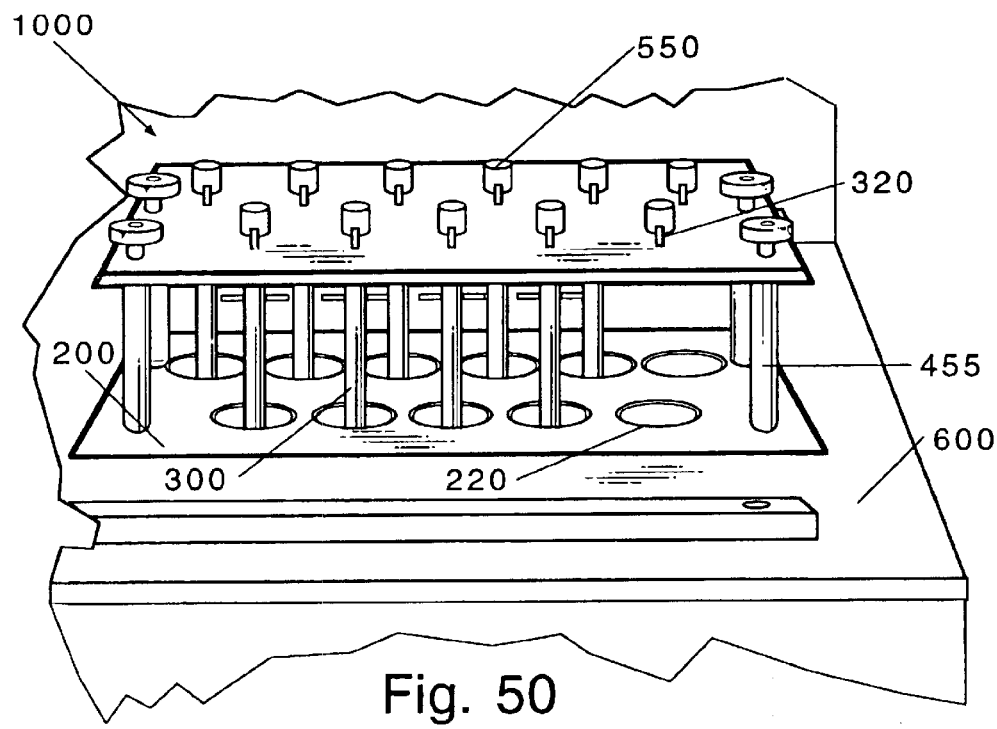

FIG. 50 is a front, top perspective view of another embodiment of a device for low temperature viscometric testing of the invention, including block (not illustrated in this view), plate, rotor, and multi-piece key, as installed in a cabinet. This device also has opposing refrigerant flowpaths and dynamic temperature control system components in its block.

Figure 51A:
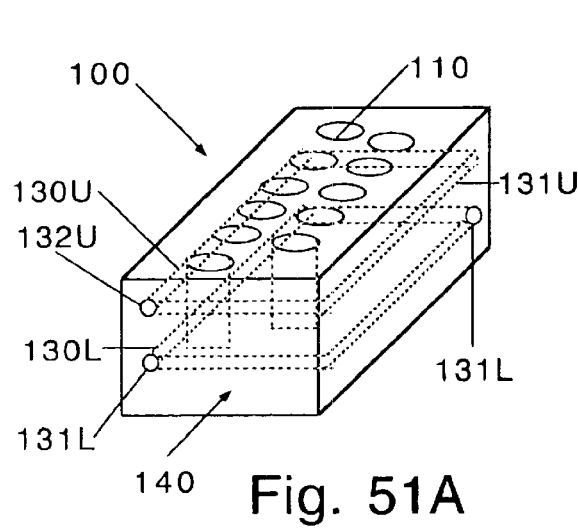
Figure 51B:
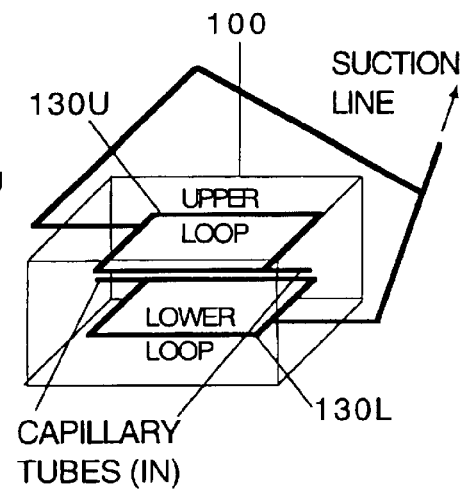

FIGS. 51A and 51B are general perspective plan views of the block for the device of FIG. 50.

Figure 52:
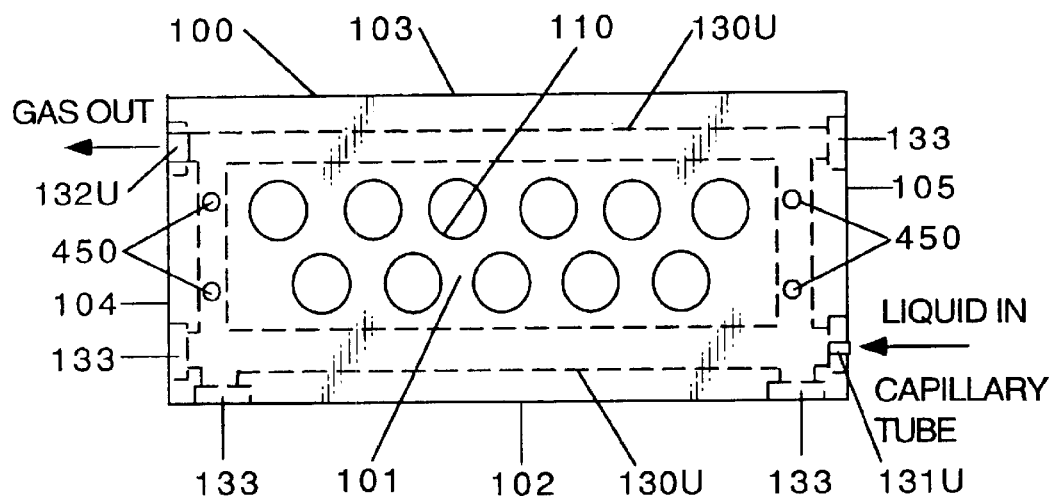

FIG. 52 is a top plan view of the block of FIG. 50, showing in particular its upper refrigeration loop.

Figure 53:
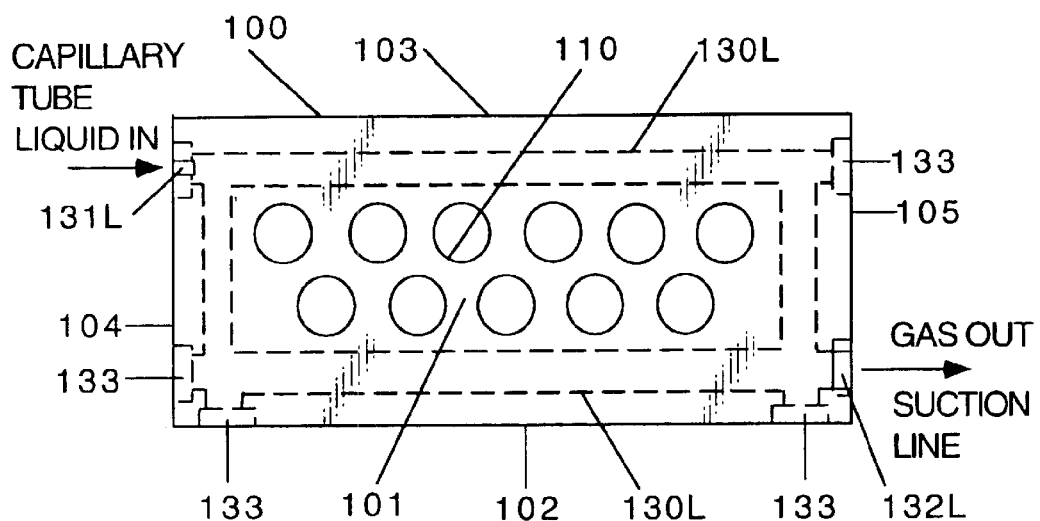

FIG. 53 is a top plan view of the block of FIG. 50, showing in particular its lower refrigeration loop.

Figure 54:
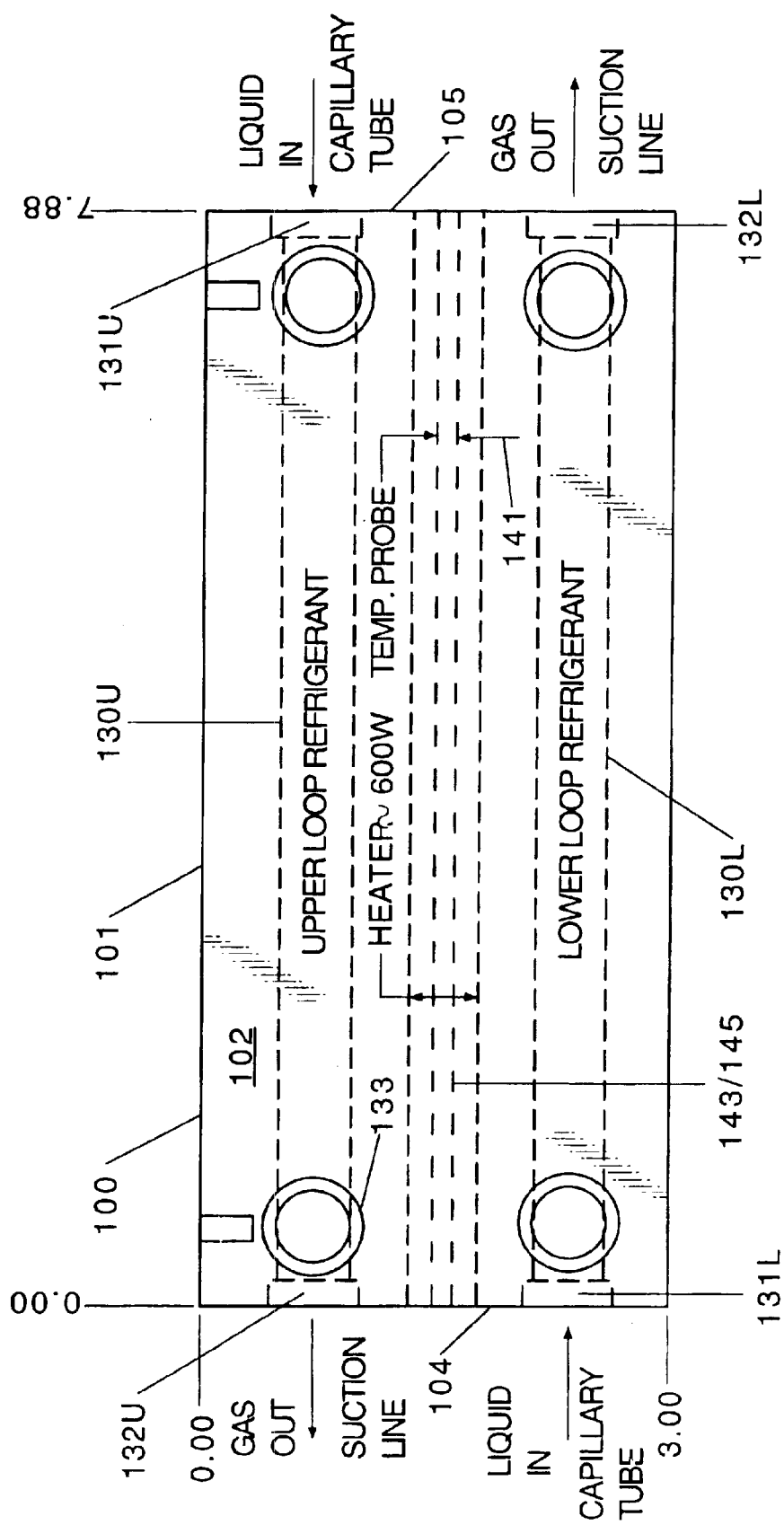

FIG. 54 is a front side plan view of the block of FIG. 50, with its cell wells not shown for the sake of clarity.

FIG. 55 is a left side plan view of the block in FIG. 50.

FIG. 56 is a right side plan view of the block in FIG. 50.

FIG. 57 is a perspective side view of a L-arm type rotor employed in the device of FIG. 50, with its dimensions otherwise and materials the same as the rotor depicted in FIGS. 10 and 42.

FIG. 58 is a side view of the rotor of FIG. 57, taken along viewing arrow 58 in FIG. 57.

Figure 59:
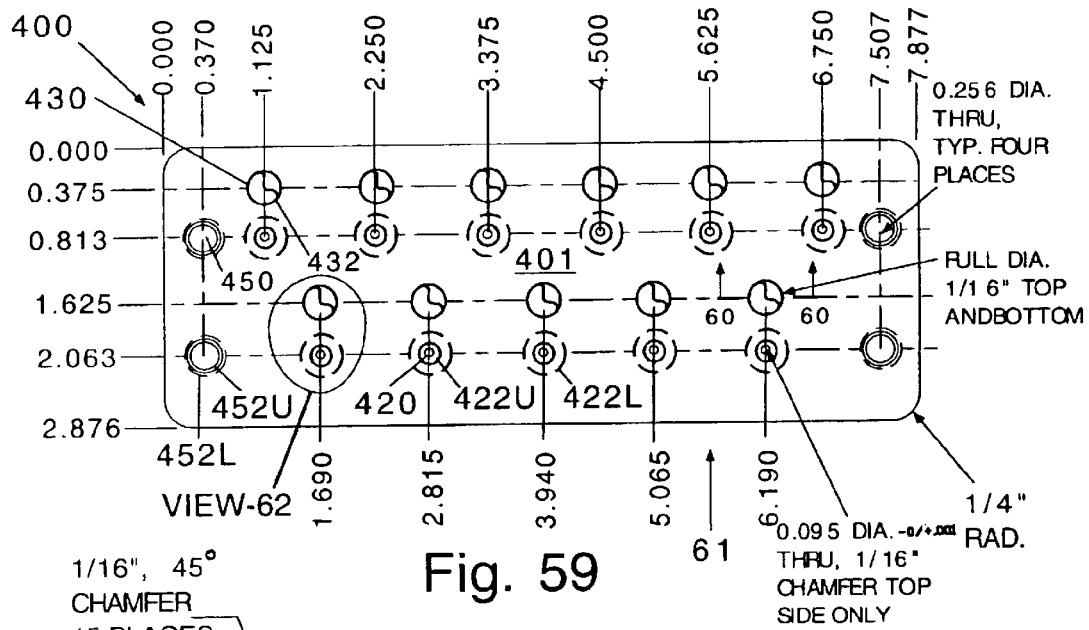

FIG. 59 is a top plan view of the top plate from the device of FIG. 50. The chamfered top bearing holes must be burr free; surface finish is #32 with all sharp edges broken.

Figure 60:
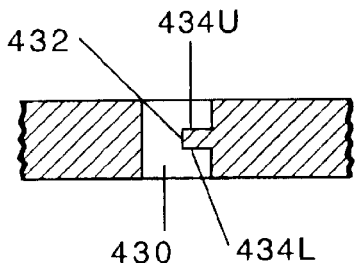

FIG. 60 is a side sectional view of part of the top plate of FIG. 59, taken along 60—60 in FIG. 59.

Figure 61:
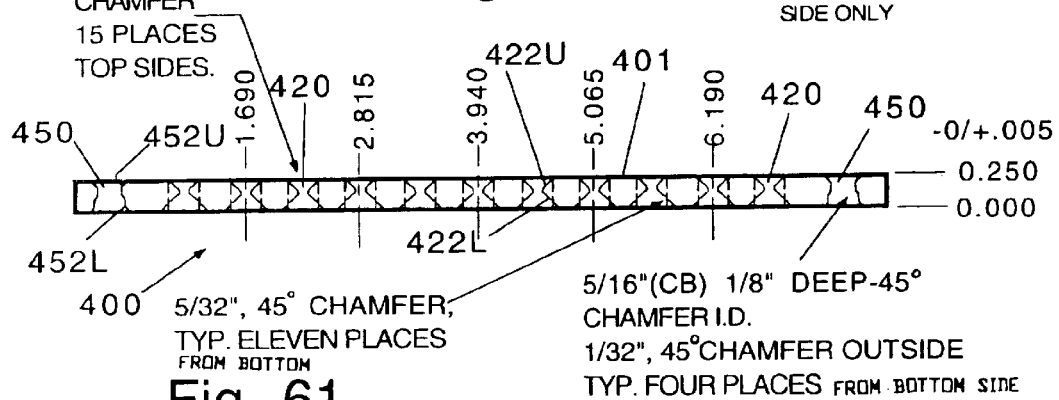

FIG. 61 is a side plan view of the top plate of FIG. 59, taken along viewing arrow 61 in FIG. 59.

Figure 62:
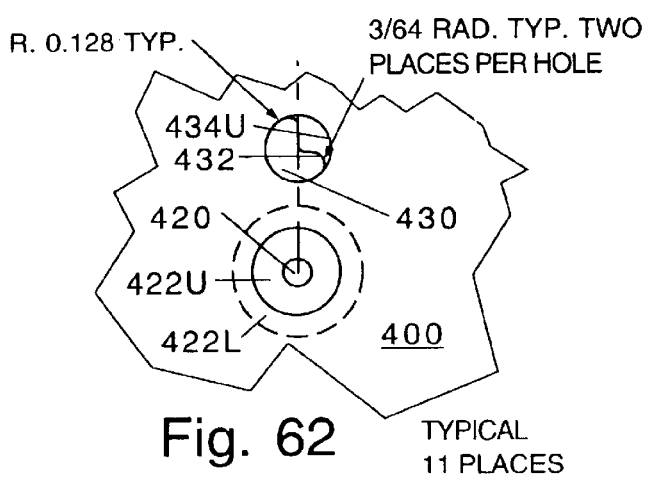
Figure 64:
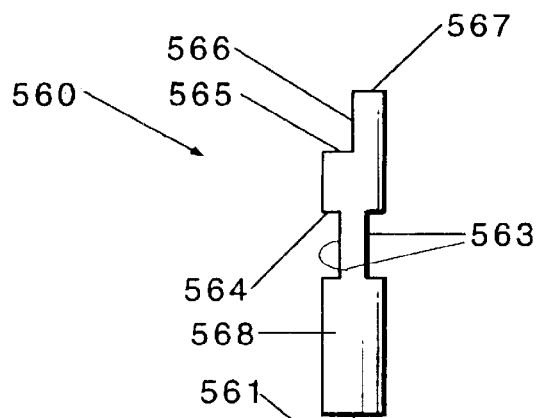
Figures 63, 66:
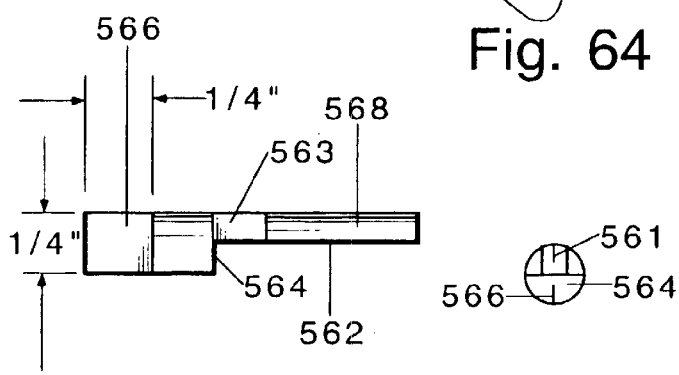
Figure 67:
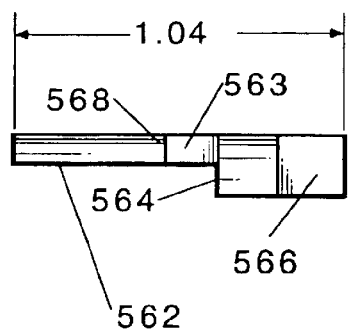
Figure 65:
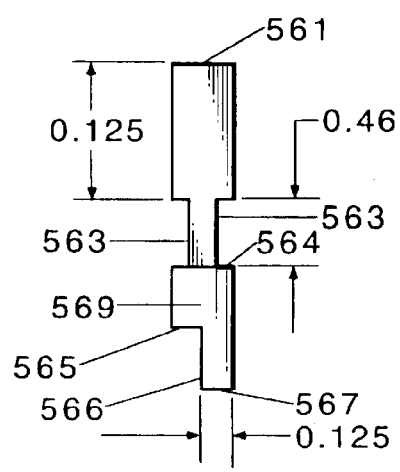
Figure 68:
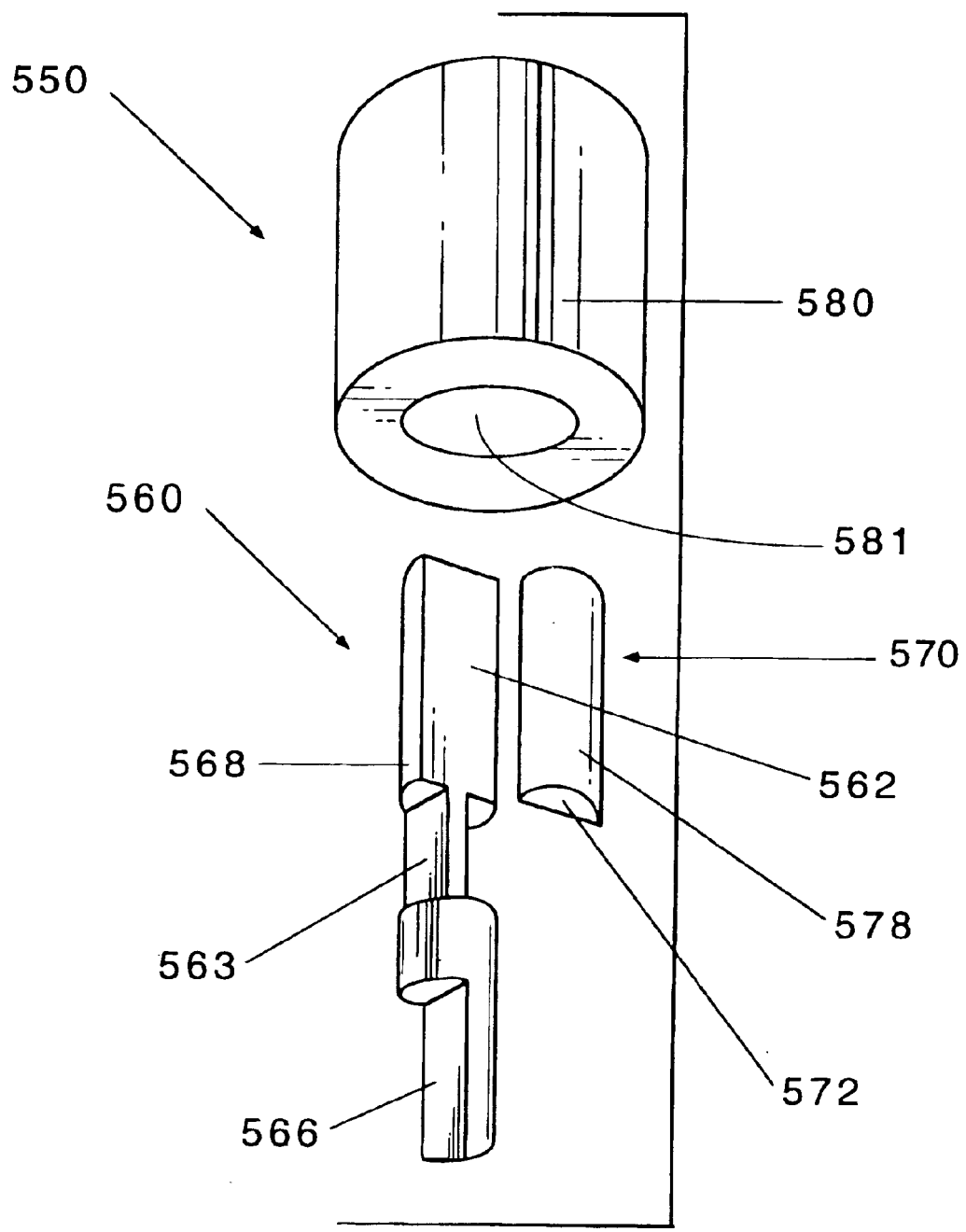

FIG. 62 is a detailed top plan view of part of the top plate of FIG. 59, taken from within circle 62 in FIG. 59.

FIGS. 63–68 are plan views of the multi-part stop key part and an exploded assembly therewith from the device of FIG. 50. Surface finish is #32 with all sharp edges broken; facing upper flat faces of the main stop key and its smaller mate, mate, and these pieces are held together by the mating cap; side cut-out stop faces orthogonal thereto form a stop, when the exploded multi-part stop key part is assembled, against the "¼-moon". stop ledge member of the top ledge in FIGS. 59–62.

Figure 69:
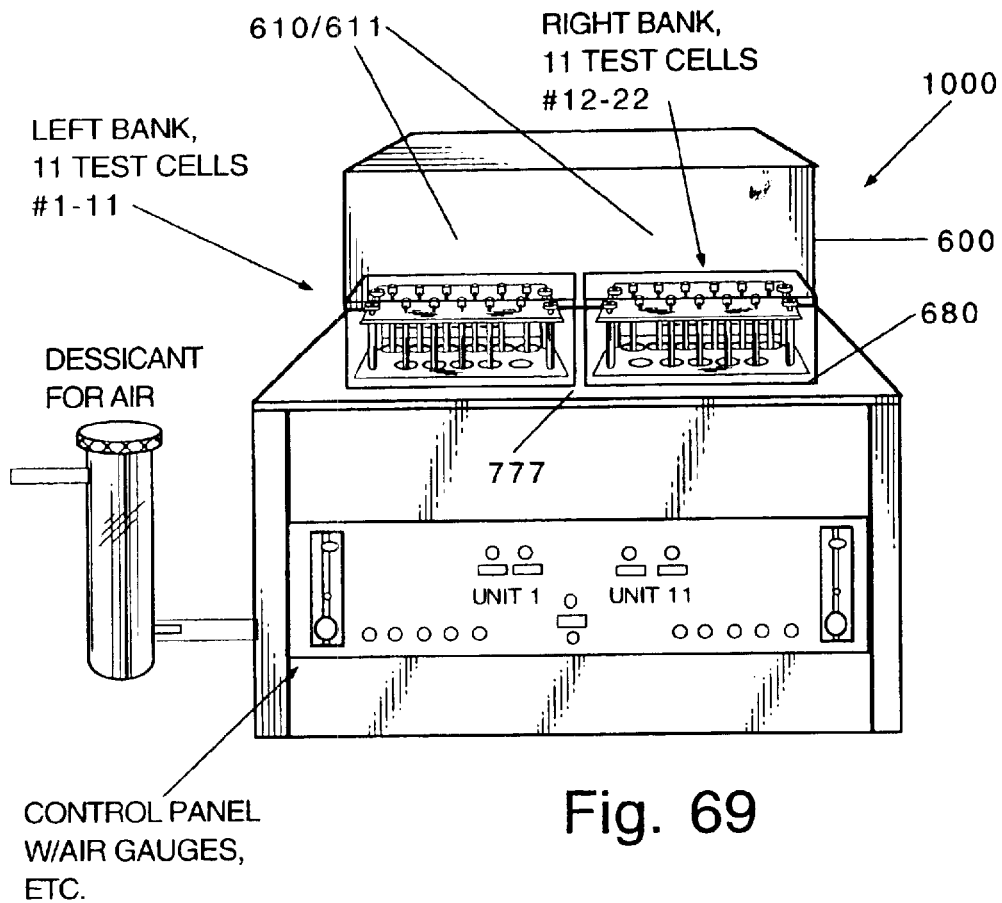

FIG. 69 is a front, perspective view of a device for viscometric testing of the invention, containing two devices as depicted in FIG. 50, in a side-by-side arrangement.

Figure 70:
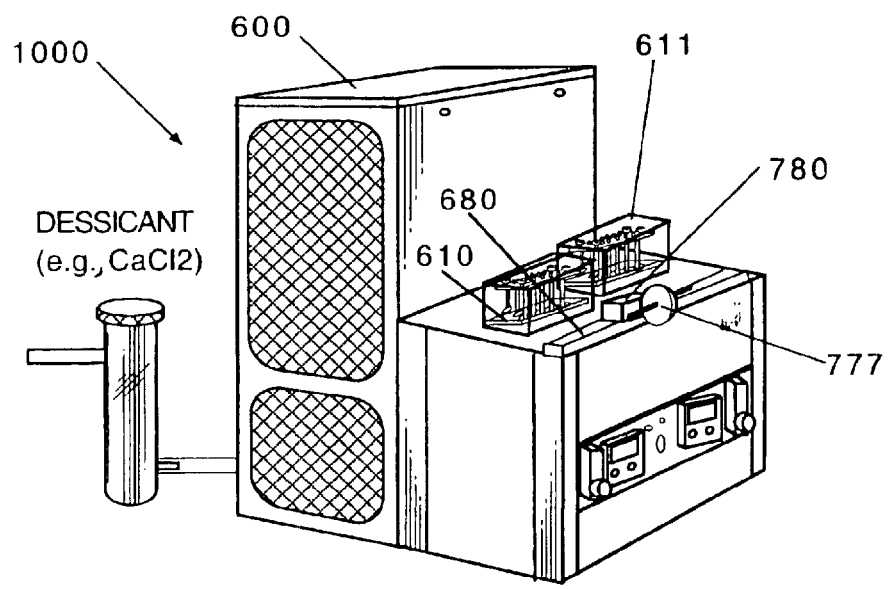

FIG. 70 is a side, perspective view of the device of FIG. 69.

Figures 71, 72, 73, 74:
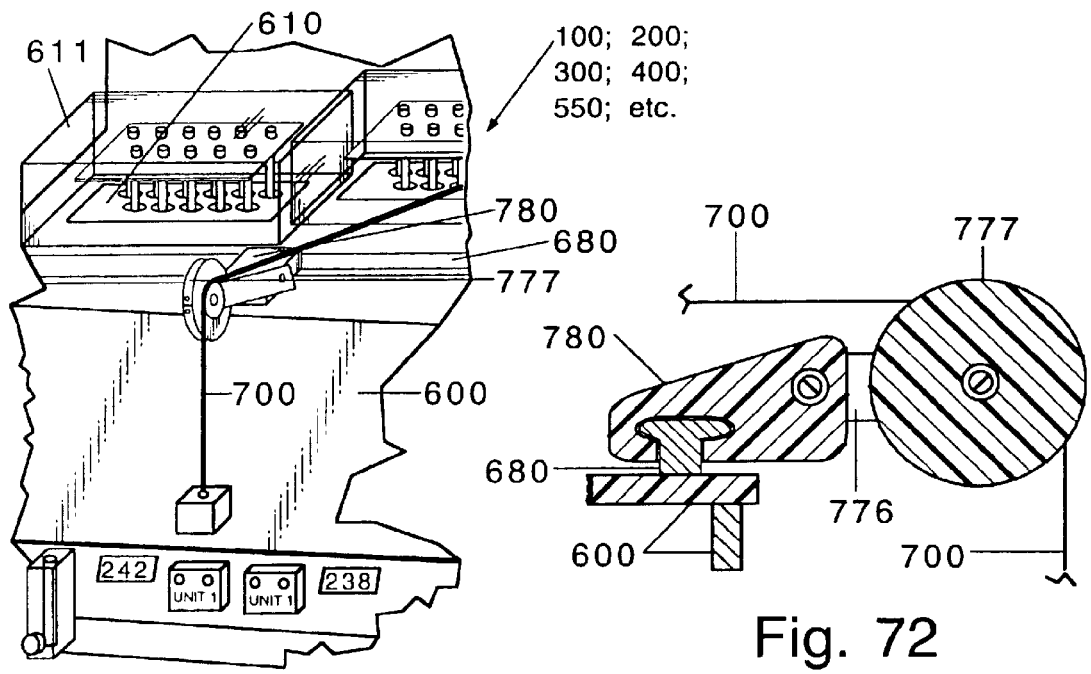

FIG. 71 is a perspective view of the counter wheel assembled with the device of FIG. 69.

FIG. 72 is a side, cutaway view of the mounted counter wheel assembly shown within FIG. 69.

FIG 73 is a side view of the counter wheel within FIG. 69. The wheel may be acid-etched; the notches are marked for counting purposes.

FIG. 74 is a front view of the counter wheel within FIG. 69.

Figure 75:
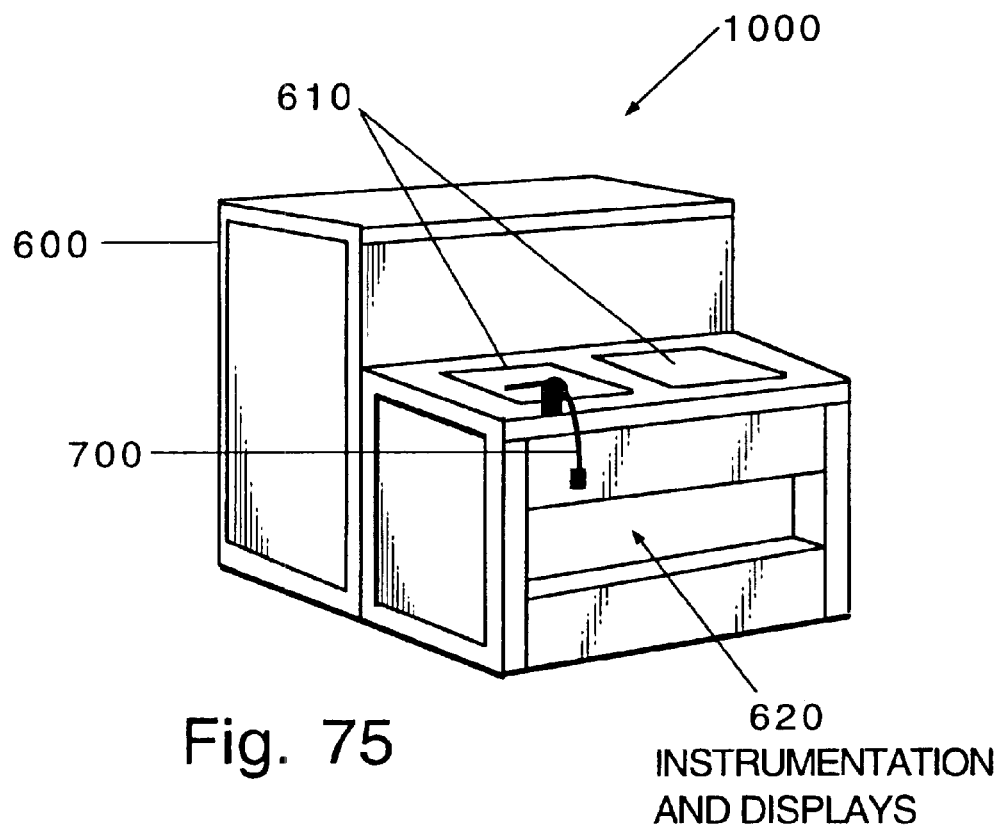

FIG. 75 is a left, top, front perspective view of a cabinet for a device for viscometric testing of the invention such as in FIG. 69, with an advantageous side by side arrangement of test cell array devices in its cabinet, in a partial stage of completion, waiting for insertion of low-temperature, oil viscosity test devices such as of FIGS. 1 and/or 50 and for instrumentation and displays.

Figure 76:
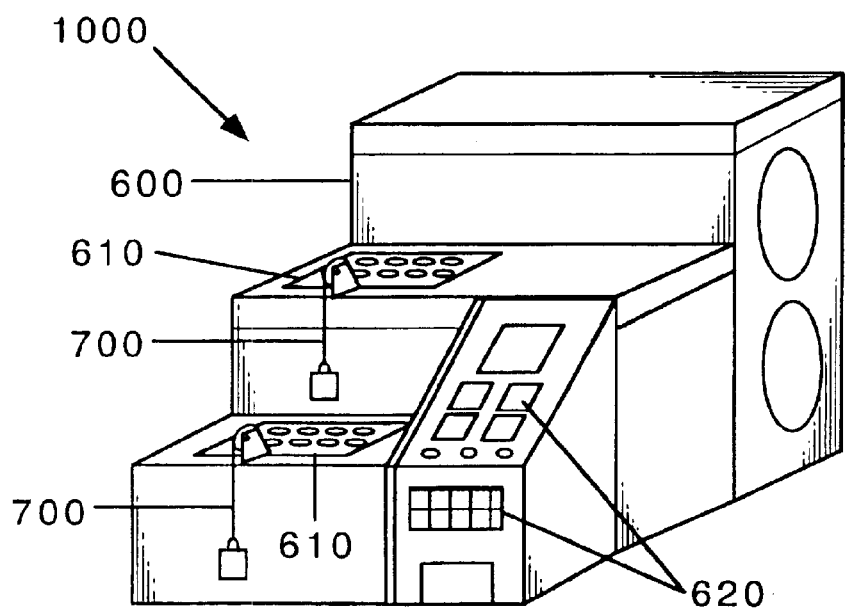

FIG. 76 is a right, top, front perspective view of another device for viscometric testing of the invention, with test cell array devices such as from FIGS. 1 and/or 50 housed in a two-tiered cabinet, one tier above the other.

Figure 77:
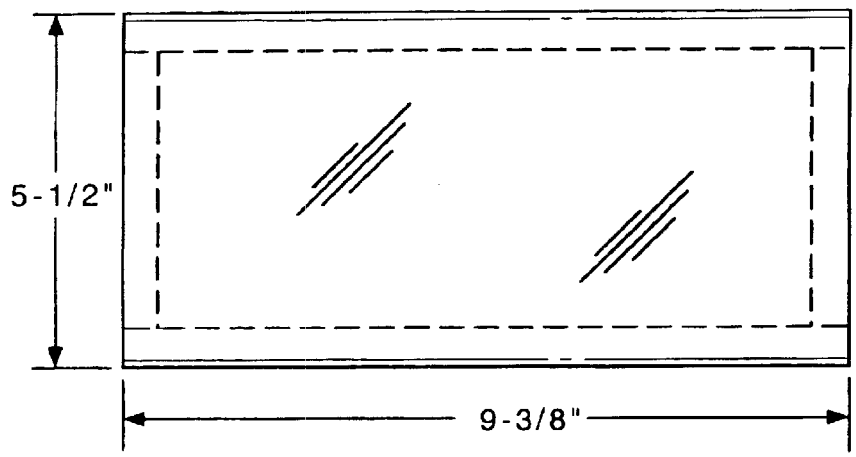

FIG. 77 is a top plan views of a see-through protective cover for a device such as of FIGS. 1 and/or FIG. 50, especially as may be provided with a cabinet such as of FIGS. 75 or 76.

Figure 78:
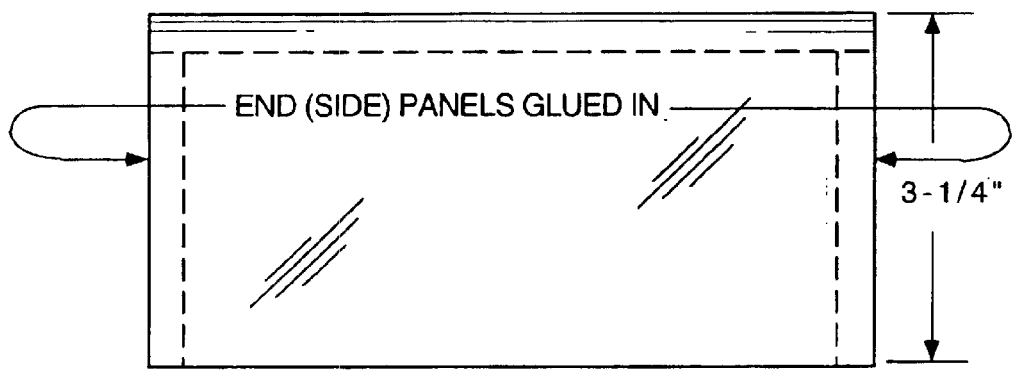

FIG. 78 is a front plan view of the cover of FIG. 77.

Figure 79:
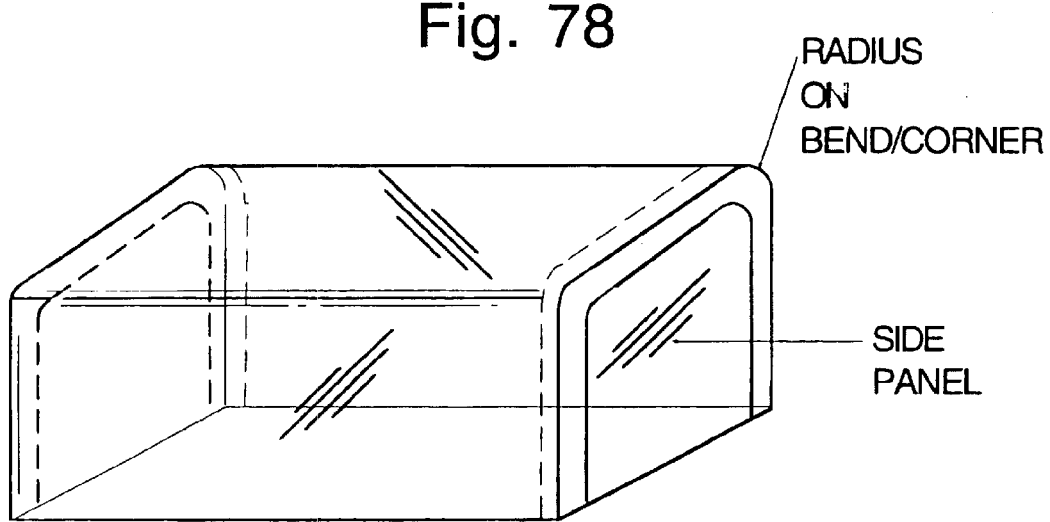
Figure 82A:
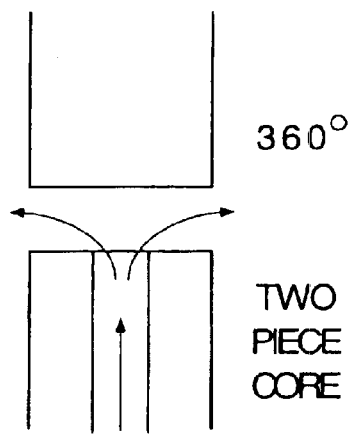
Figure 82B:
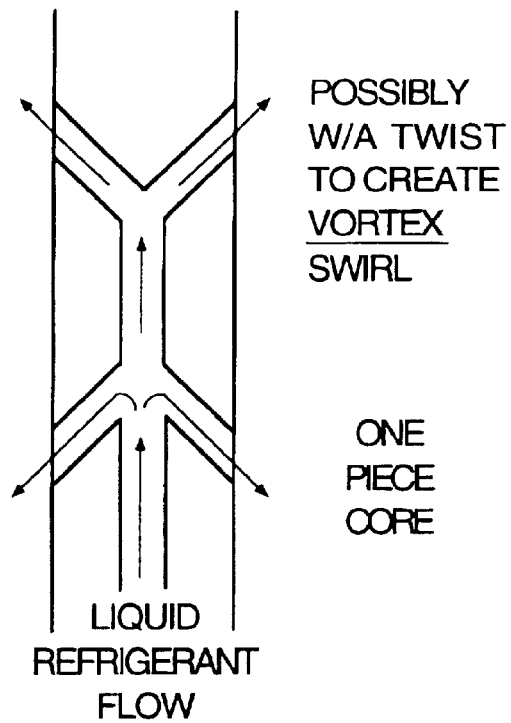
Figure 82C:
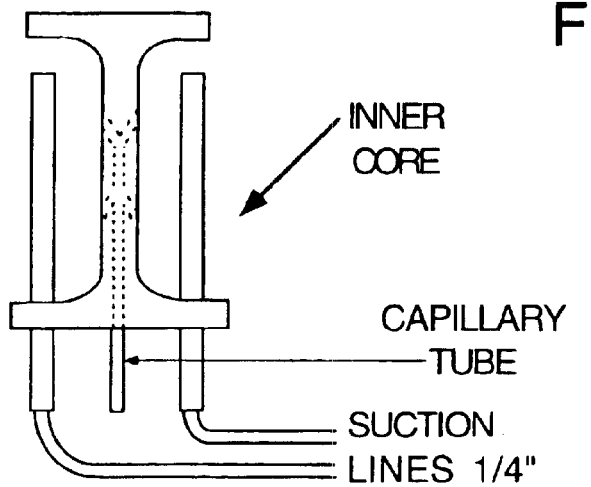
Figure 82E:
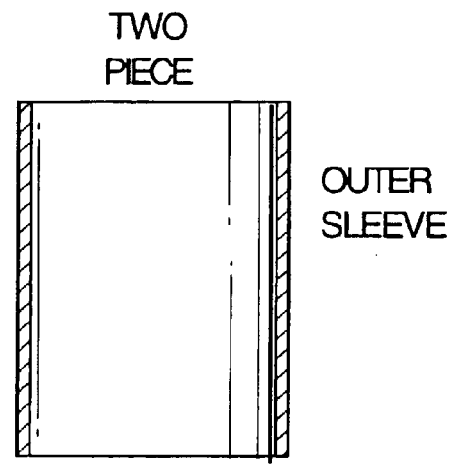
Figure 82D:
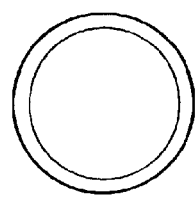

FIG. 79 is a perspective plan view of the cover of FIG. 77.

FIG. 80 is a top plan view of an embodiment of the invention having a radially endowed heat-conductable solid member (block) and a hexagonal test port pattern. This embodiment is especially useful in TP-1 testing as well as being useful for other test methods such as in Scanning Brookfield Testing; air Brookfield testing; Theological testing, as in a dynamometer, and so forth, owing to its modular central evaporator unit surrounded by its annular copper test cell block (bank) subunit, where the one evaporator core provides for the many options for the outer ring. The radial configuration ensures that the heat or cold load on each sample is the same, and that the incoming heat remains the same on the bank when cooling. Note that the same amount of heat which is coming in is the amount of heat being rejected (left over) from the main heater-evaporator interface, and instead of having two cold fronts and two heat fronts such as in the rectangular block, control can be effected an easy way with heat that combines the two heat fronts together. Sensor locations can be up front between every sample for monitoring.

FIG. 81 (A, B) shows side plan views of the embodiment of FIG. 80, with parts of the FIGS. 81A and 81B in partial section. The temperature sensor is located on the same circumference of the circle as the center of the test cells, with the inner core, for example, being radially symmetrical, say, with circular or cylindrical type walls. Note, the donut-shaped test block; the inner heating-cooling core, where the heater acts as a buffer, only requiring as much heat to warm as heat coming in; and two heat fronts colliding together.

FIG. 82 (A-E) shows views of parts of two-piece cores, which may be employed in an embodiment such as that of FIG. 80, with A, B, C and E from the side, and D from the top. The evaporator core is equal to the IN volume, $5^{13}/_8$" I.D.

soft copper, and the outer sleeve is $^1/_{16}$" to $^1/_8$" thick copper or stainless steel, with the stainless steel to act as a buffer. Note, a benefit of this embodiment is that it would create only one cold spot at the exact center of the core.

Figure 83:
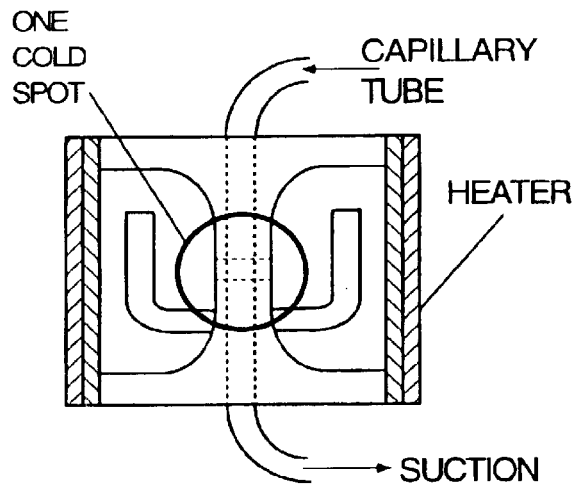

FIG. 83 is a side plan view of another round block and core embodiment which may be employed in an embodiment such as that of FIG. 80. The heater may be thick or a thin film, metal or nonmetallic. Suction occurs at the bottom.

Figure 84A:
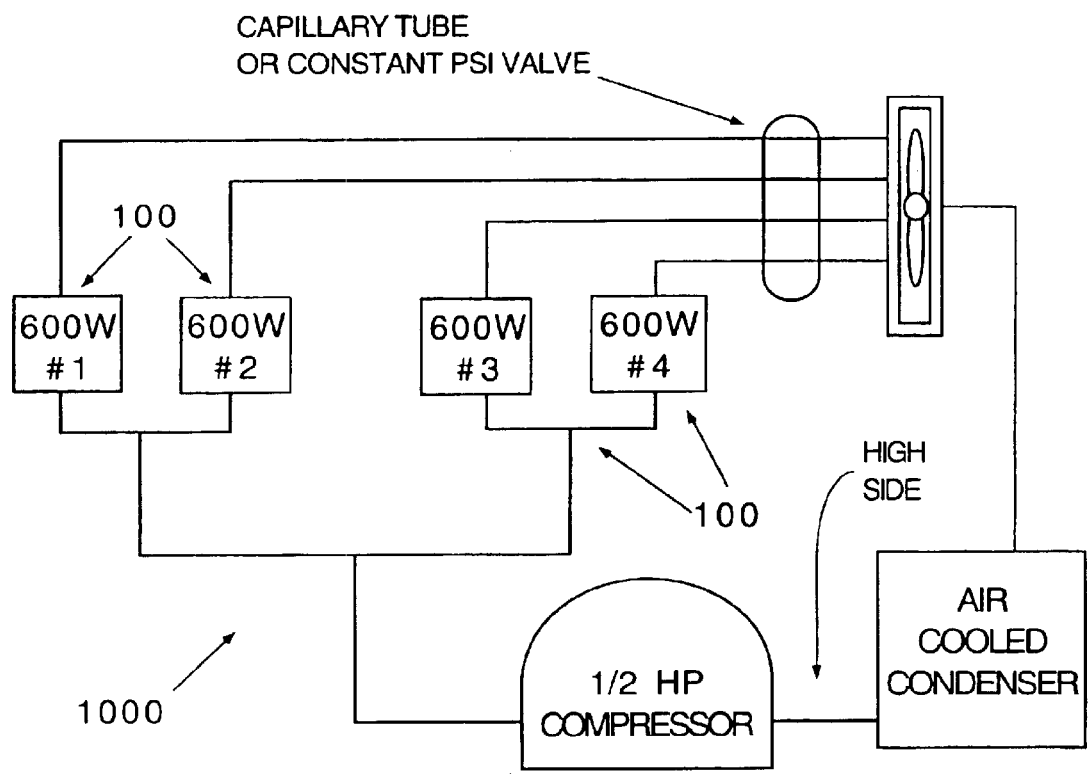

FIG. 84 (A, B) shows plan views of refrigerant supply lines for an instrumental array of four blocks such as those from FIGS. 1, 50 and/or 80, with FIG. 84A being a "parallel" and FIG. 84B a "series" configuration. The manifold (FIG. 84B) optionally may be a gate which is a rotating gate, for example, with a stepping motor; magnetic stirrer; or turbine—to ameliorate the "twitter effect" of one or two blocks being colder than the others, say, from atomic "clumping." The configuration in series (FIG. 84B) solves the problem of multiple temperature systems and flow problems in comparison to the "octopus" style, in parallel configuration (FIGS. 84A and 86) where the twitter effect can occur. The alternate system with opposing flowpath (FIG. 84B) may ameliorate single series flowpath characteristic of cold to less cold blocks, and, in such a system, the refrigerant could be pumped with the same pump and system, or be a separate system.

Figure 86:
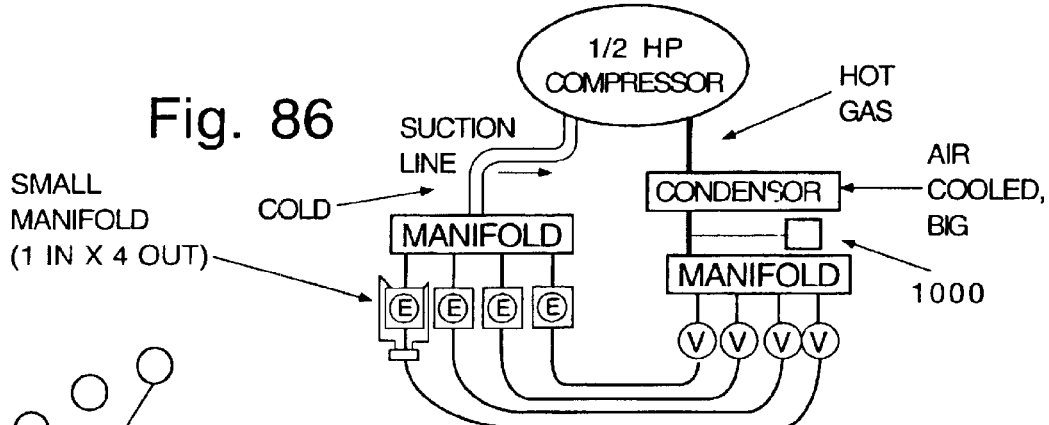
Figure 87A:
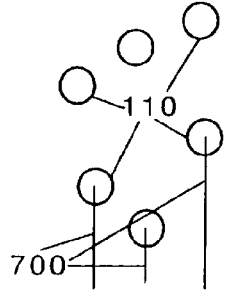
Figure 87B:
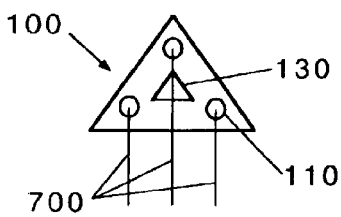
Figure 87C:
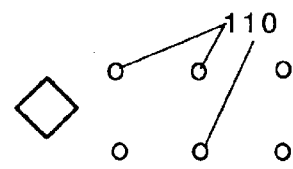
Figure 87D:
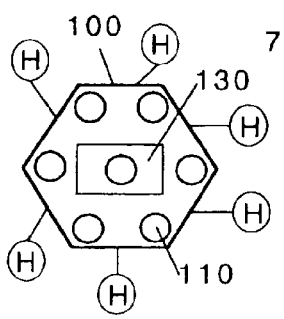
Figure 87E:
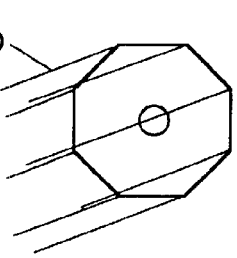
Figure 87F:
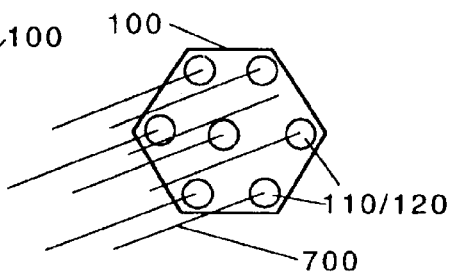
Figure 87G:
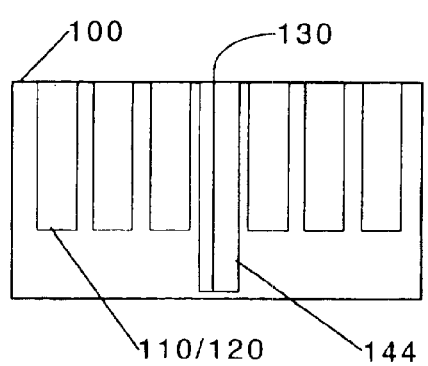
Figure 87H:
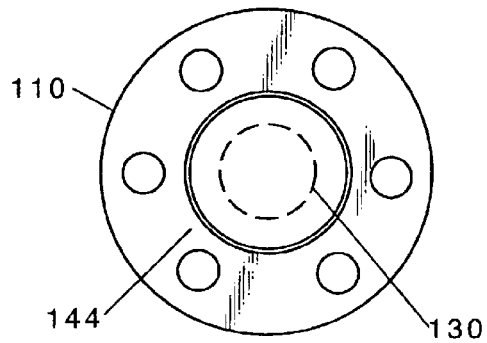
Figure 87I:
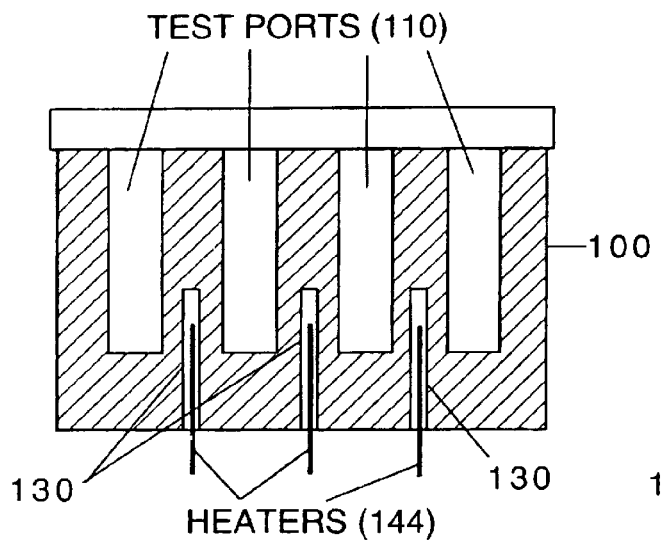
Figure 87J:
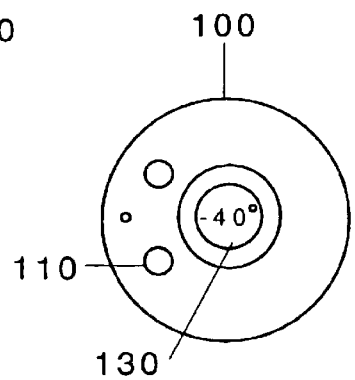
Figure 87K:
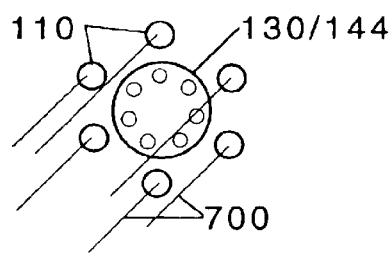
Figure 87L:
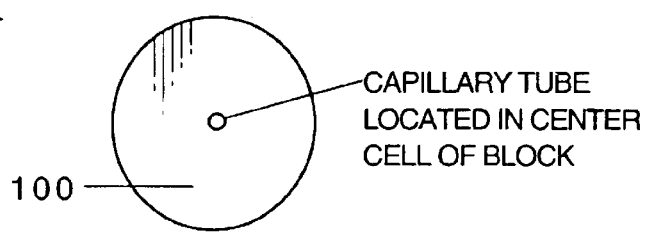
Figure 87M:
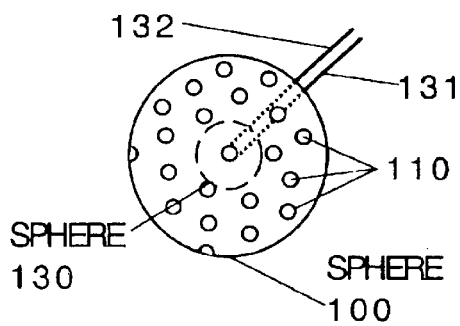
Figure 87N:
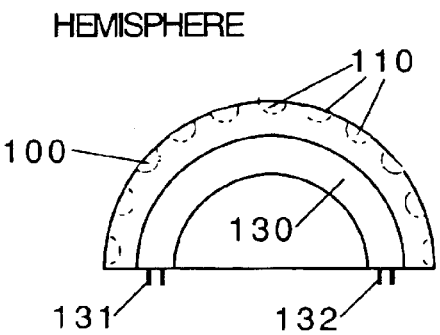

FIG. 85 (A–C) shows top (FIG. 85A), side (FIG. 85B) and unmachined block (FIG. 85C) views of another form of block, a rectangular box, in partial stages of completion, which, particularly when completed, is also useful in an instrumental array such as those of FIGS. 69, 84 and 86.

FIG. 86 is a plan view of another "parallel" type system of refrigerant supply lines for an instrumental array of four blocks for TP-1 testing. The two main manifolds could be in the same assembly separated by DELRIN plastic standoffs; a valve (V) may be wired to open and close (with maximum temperature capacity).

FIG. 87 (A–N) shows plan views for blocks and/or test well arrays, some in partial stages of completion, particularly as may be employed in TP-1 testing. Generally, test cells can include hexagon-shaped arrays or round blocks; capillary tube(s) serve(s) as input, and a suction line serves as exit, and a lower loop with a 180-degree opposing flowpath may be provided for reverse flow (FIG. 87D); a thin film heater can completely surround evaporator unit to provide even heating and cooling (FIG. 87H); joints may be silver soldered, and a stainless steel cup and 0.001" air gap acts as (air) insulation, plus oil and cup acts as heat flow buffer (FIG. 87I); with a hexagonal configuration, there may be six test lines, and 600W output by 100W heaters, which may be inexpensive (FIG. 87K); with a capillary tube in the center of a block, there may be one cold spot, and radial heat flow can maximize the heat flow control with a radial center (FIG. 87L); spherical or hemispherical blocks may be employed (FIGS. 87M and 87N).

Figure 88:
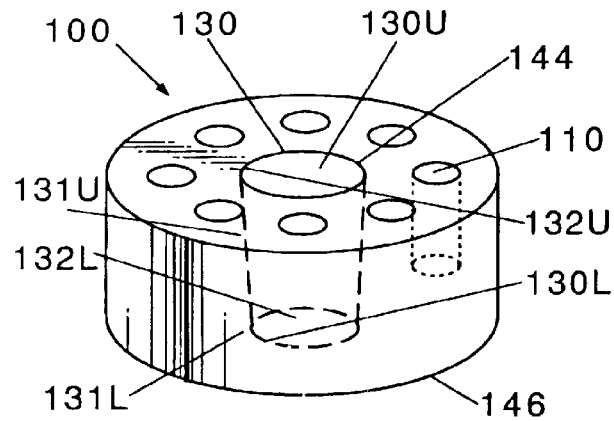

FIG. 88 is a perspective plan view of another embodiment of the invention having a radially endowed, heat-conductable, solid member with upper and lower opposing flow paths. Heating element (inner) (first) is alternate or option, and an outer surface could be a heating element (second) (or be placed in a heat bath).

Figure 89:
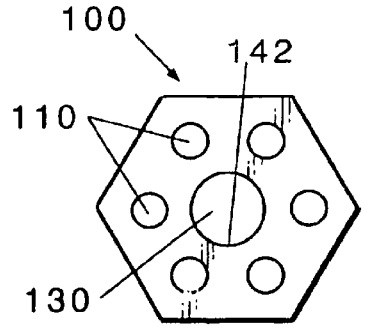

FIG. 89 is a top view of another embodiment of the invention.

Figure 90:
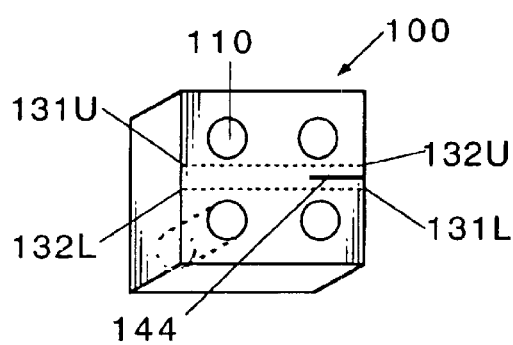

FIG. 90 is a perspective plan view of another embodiment of the invention, which has opposing flow path refrigeration.

Figure 91:
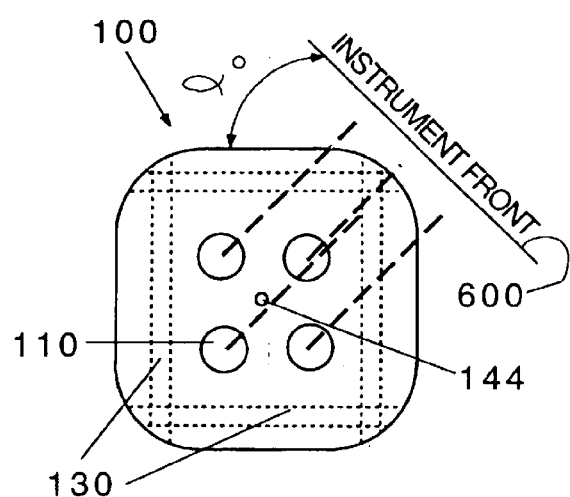

FIG. 91 is a top plan view of another inventive embodiment, in which angled installation with respect to the instrument front is employed. The heavy dashed lines shown represent the paths TP-1 strings will take when the unit is installed with the housing.

Figure 92:
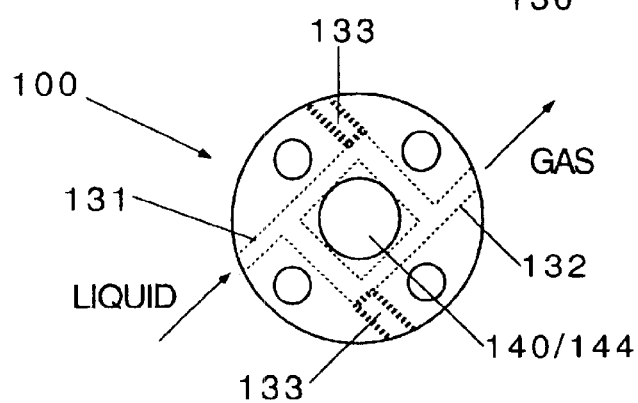

FIG. 92 is a top plan view of another inventive embodiment.

Figure 93:
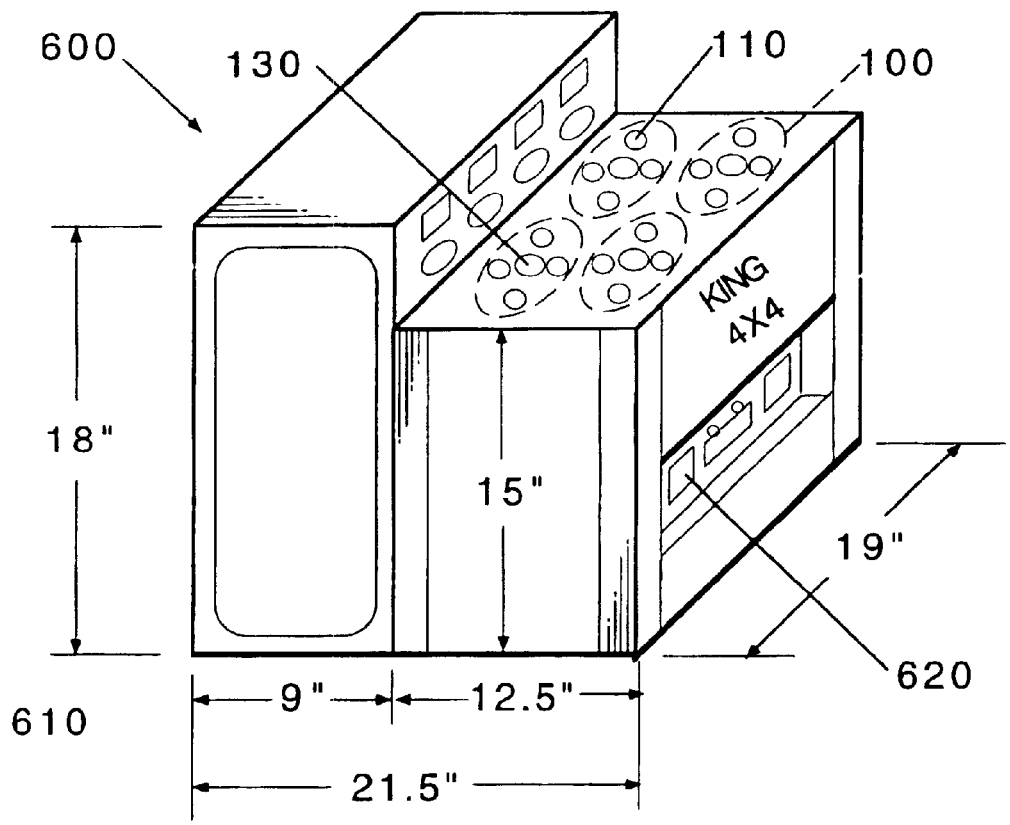

FIG. 93 is a perspective plan view of an embodiment of the invention which is a low temperature, oil-testing instrument having an array of cylindrical test banks. Generally, about 600W per block is a minimum; a dual condenser coil may be employed, and the instrument can be adapted for Scanning Brookfield Testing; ASTM D-97 testing; and MRV/TP1 testing. Dimensions are indicated in FIG. 93, with the large side opening (left hand side) having 3" corner radii with a 20-18 open screen for strength.

Figure 94:
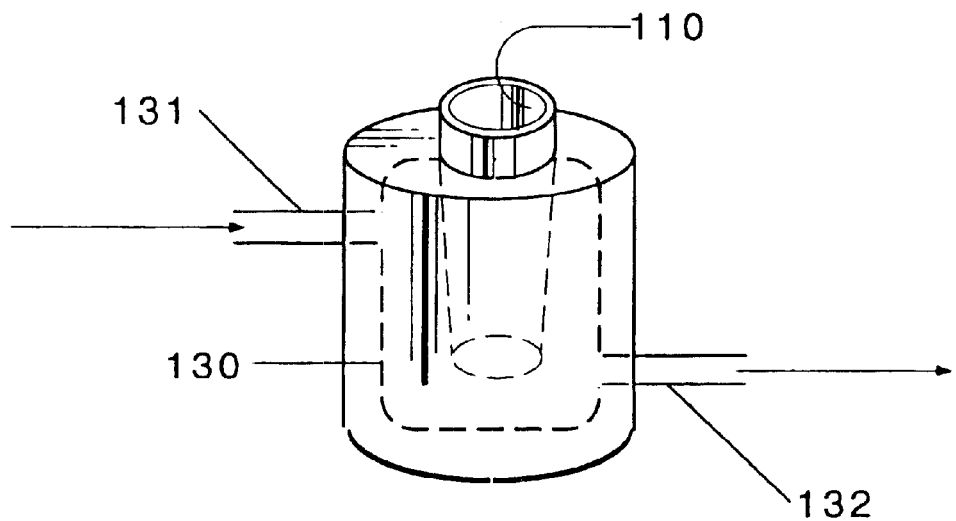

FIG. 94 is a perspective plan view of another embodiment of the invention having a single, directly cooled test cell, which may be employed alone or in an array in which each test cell may be cooled/controlled independently to a particular temperature.

Figure 95:
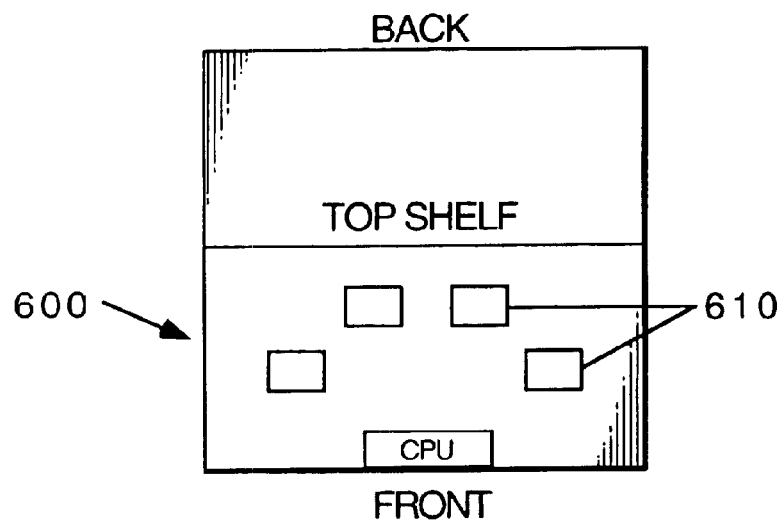

FIG. 95 is a top plan view of an embodiment of the invention which is a low temperature, oil-testing instrument with an array of rectangular box test banks, otherwise similar to FIG. 94.

Figure 96:
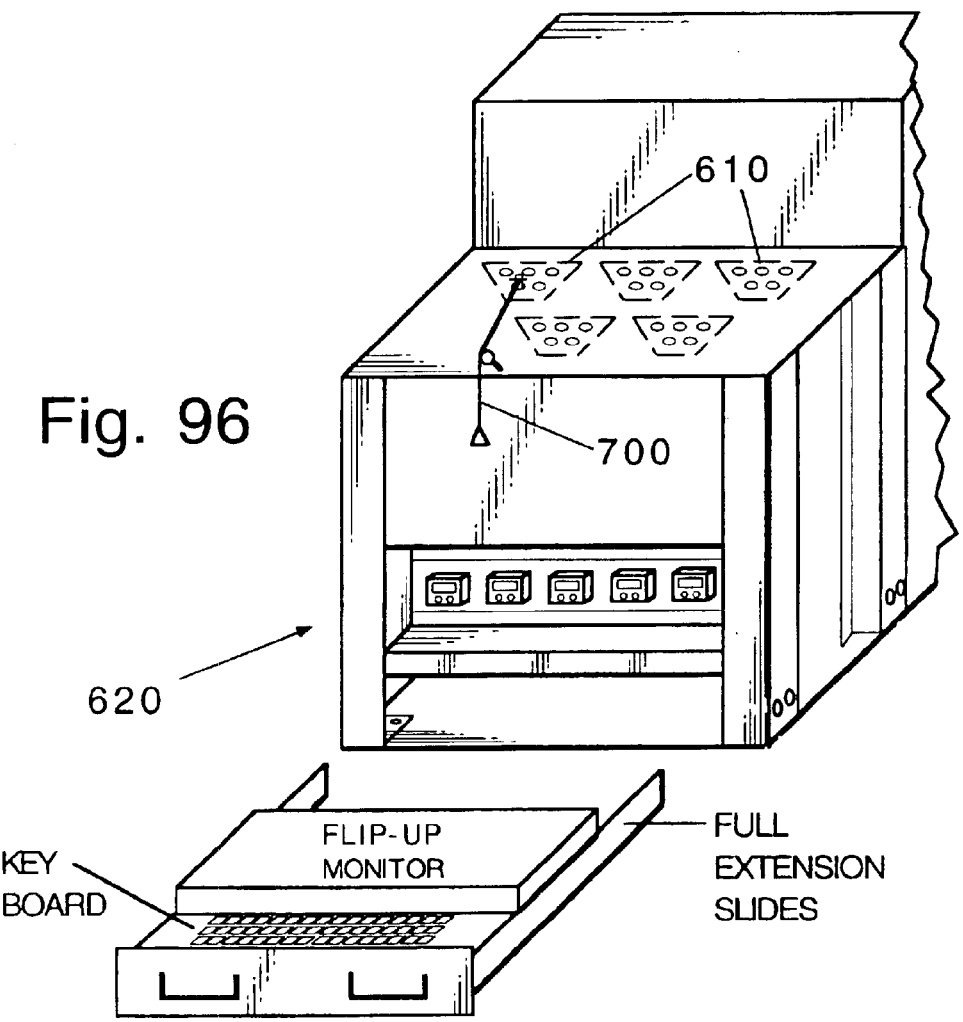

FIG. 96 is a perspective plan view of an embodiment of the invention which is a low temperature, oil-testing instrument having an array of pentagonal box test banks.

Figure 97:
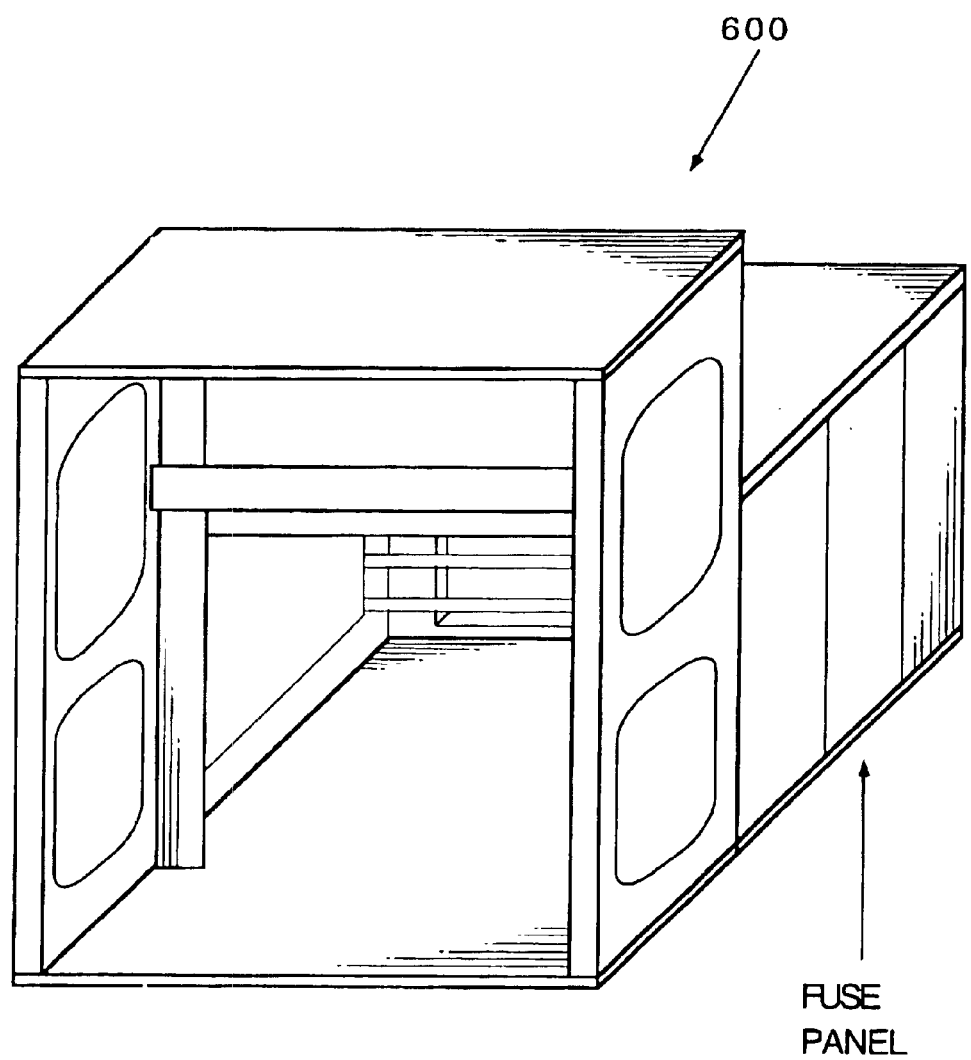

FIG. 97 is a rear perspective view of a cabinet member which may be employed with the blocks of the invention for TP-1 testing as well as for other types of testing set ups.

Figure 98:
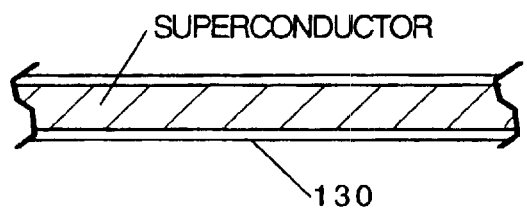

FIG. 98 is a side view of the invention as applied to direct cooling of a superconducting material.

Figure 99:
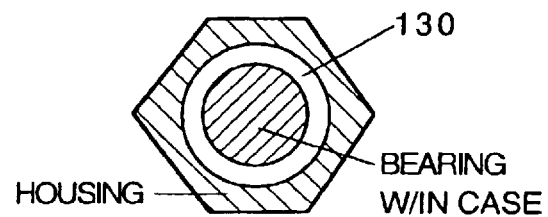

FIG. 99 is a side view of the invention as applied to direct cooling of a heat-releasing mechanical item, here, a bearing.

Figure 100:
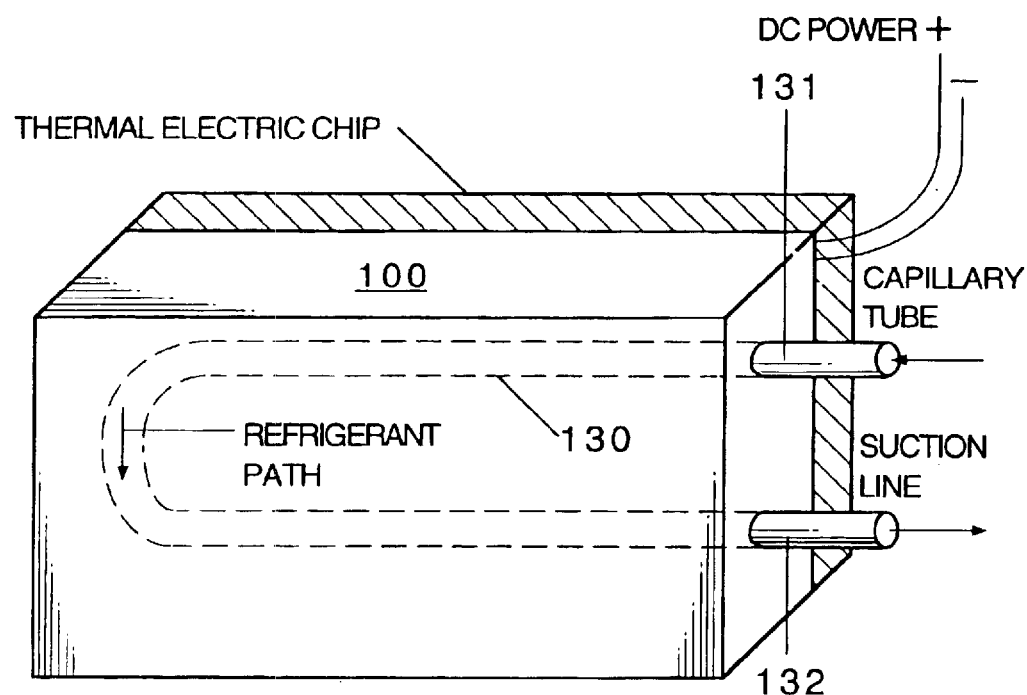

FIG. 100 is a perspective plan view of the invention as applied to direct cooling of a heat-releasing electronic item, here, a thermal electric chip. Generally, thermal electric chips can be used as heaters or coolers by reversing the power; the block can be made from copper or other material that has good conduction properties; temperature control for the refrigerant (heat sink) could be maintained by refrigeration-system, low-side pressure; and more than one capillary tube and suction line may be needed. Also note that the solid heat sink can have refrigerant running directly from a compressor through a line bored through the heat sink; it is beneficial, as no cooling liquid is needed; the system can be run with the refrigerator system close to the operational, set temperature, and, to plus or minus forty degrees Fahrenheit, the thermal electric chip can be allowed to actually control the temperature by reversing the heating or cooling (voltage). A CPU chip can be cooled analogously.

ADDITIONAL DETAIL FURTHER ILLUSTRATIVE OF THE INVENTION

The invention can be further understood by the present detail which may be read in view of the drawings. The same is to be taken in an illustrative and not necessarily limiting sense.

The following table lists and identifies some features of the invention 1000 as depicted in the drawings:

Feature Comment

100 Refrigeration test block, beneficially of free-machining copper.
101 Top surface of the block.
102 Front surface of the block.
103 Rear surface of the block.
104 Left side surface of the block.
105 Right side surface of the block.
110 Cell wells, which may be countersunk at the bottom, say, about 0.005 of an inch, so that should sand or other small debris fall in, a sample sleeve (test cell) will still fit to the proper, full height.
111 Cell well internal sleeves (extensions), e.g., with seam or seamless for better fit (stainless steel), which may be glued, welded, press-fit, or otherwise maintained in place.
112 Dry gas inlet, with the gas able to be, for example, air, nitrogen, argon, and so forth, and which may be provided under pressure through the inlet.
113 Bond, say, of glue.
120 Test cell sleeve constructions (test cells).
121 Test cell cylinder, e.g., #304-stainless steel.
122 Test cell bottom plug, e.g., #304 stainless steel.
123 Test cell radially endowed pin, e.g., carbide.
124 Cylinder flat side for air release for easy removal and insertion of the test cells.
125 Test cell sleeve J-slots for easy removal of the test cell with T-wrench.
126 T-tools (T-wrenches).
126D Dug-out portion of shaft of dug-out T-wrench, say, having generally cylindrical shape. The dug-out T-wrench can assist in removal of the test cell insert sleeves of the invention without it being necessary to remove the rotor from the test cell.
126F Flat portion to shaft of dug-out T-wrench.
126H Handle of T-wrench, for instance, made of plastic resin 126HR, e.g., DELRIN plastic; or metal 126HM, e.g., stainless steel.
126P Opposing pins, for example, of stainless steel, to engage J-grooves of test cell cylinder.
126S Shaft of T-wrench, for instance, made of plastic resin 126SR, e.g., DELRIN plastic; or metal 126SM, e.g., stainless steel.
126T Tip of T-wrench, for instance, made of plastic resin 126TR, e.g., DELRIN plastic, or of metal, etc.
126W Wrap-around, slightly enveloping portion to tip in dug-out T-wrench.
130 Block refrigerant pathway, for example, 42-inch net length in one-way flowpath block.
130U Block refrigerant upper pathway.
130L Block refrigerant lower pathway.
131 Block refrigerant pathway entry.
131U Block refrigerant upper pathway entry.
131L Block refrigerant lower pathway entry.
132 Block refrigerant pathway exit.
132U Block refrigerant upper pathway exit.
132L Block refrigerant lower pathway exit.
133 Block refrigerant pathway construction bore plugs.
139 Refrigerant supply to block.
140 Dynamic temperature-control system.
141 Temperature sensor channel in block, for example, which in the rectangular solid block is beneficially fit precisely in the center of the block for very accurate readout and control.
142 Electronic temperature sensor.
143 First heater channel in block, which may have a blind end or may be drilled through the block so that a heater may be inserted from either end of the block, as may be desired, with plugging of the non-insertion (far) end.
143L Heater space with lower shoulder for heater to rest upon.
144 First electric heater, e.g., 600-watt capacity. or more or less, as desired or otherwise suitable.
145 Second heater channel in block, which also may have a blind end or may be drilled through the block so that a heater may be inserted from either end of the block, as may be desired, with plugging of the far end.
146 Second electric heater, e.g., 600-watt capacity, or more or less, as desired or otherwise suitable.
147 Channel plugs.
149 Electric/electronic temperature-control source.
150 Internal stand-offs, for example, of DELRIN plastic, drilled to 0.201-inch diameter and tapped to ¼-20 thread, fully threaded.
151 Stand-off hole, for example, drilled to 0.201-inch diameter and tapped to ¼-20 thread to accommodate connecting studs for the internal stand-offs.
200 Intermediate top plate insert, for example, of a suitable plastic such as DELRIN plastic.
201 Top surface of intermediate top plate insert.
210 Dry gas distribution channel in top plate insert.
212 Dry gas side channel and exit to test cell.
218 Sealing gasket for securing to the insert to enclose the dry gas distribution channels, for instance, of metal foil or plastic, say, with adhesive backing for attachment, e.g., adhesive-backed aluminum foil.
220 Test cell orifice.
222 Chamfer in orifice top for ease of insertion of test cell sleeve.
224 Shoulder in orifice bottom to receive cell well extensions, e.g., insert glued to extension here.
250 Stand-off holes.
300 Test rotor.
310 Test rotor generally cylindrical shaft, e.g., #PH 17-4 stainless steel.
320 Test rotor top bearing.
323 Test rotor radially endowed cup, say, having conical flare from cup radius to mouth to ensure correct and easy placement of test rotor over pin, e.g., carbide coated also (friction properties improve with use).
330 Test rotor stop arm.
331 Stop arm test string set-up assistance hook, for example, positioned at about 11-o'clock.
340 Test rotor heat transmission restriction neck.
350 Test rotor test drum (may be interchangeable), e.g., DELRIN plastic.
400 Top plate, e.g., #303/304 stainless steel.
401 Top surface of the top plate.
420 Top bearing holes.
422 Top bearing hole chamfers.
422U Top bearing hole upper chamfers.
422L Top bearing hole lower chamfers.
430 Stop key holes.
431 Stop key hole threaded access holes.
432 Stop ledge for multi-part key.
434U Upper stop ledge cut-out.
434L Lower stop ledge cut-out.
450 Stand-off holes.
452 Stand-off hole chamfers.
452U Stand-off hole upper chamfer.
452L Stand-off hole lower chamfer.
455 Top stand-offs, for example, of stainless steel, which go between the top plate insert and top plate.
456 Threaded ends to top stand-offs.
500 One-piece stop key, e.g., of #303/304 stainless steel.
510 Stop key generally cylindrical shaft.
520 Stop notch, middle.
522 Middle notch face.
530 Rotor arm stop notch, bottom.
532 Bottom stop notch face, e.g., planarly perpendicular with respect to the middle notch face 522.
550 Multi-piece stop key, e.g., of stainless steel and DELRIN plastic components.
560 Main stop key piece, e.g., of stainless steel.
561 Main stop key piece top end.
562 Main stop key piece top, inner flat face.
563 Main stop key piece side cut-out stop faces, e.g., each planarly perpendicular to the flat face 562.
564 Main stop key piece upper facing shoulder for engaging the lower surface of the top plate.
565 Main stop key piece lower facing shoulder.
566 Main stop key piece rotor stop arm engaging face, e.g., planarly perpendicular to the flat face 562.
567 Main stop key bottom end.
568 Main stop key major round outside surface.
569 Main stop key minor round outside surface.
570 Stop key top face mate, e.g., of stainless steel and semicylindrically shaped.
571 Stop key top face mate, flat face.
578 Stop key top face mate, round outside surface.
580 Stop key mating cap, e.g., of DELRIN plastic.
581 Stop key mating cap, blind hole for insertion of mated main stop key piece and its mate after the main piece has been inserted up through the stop key hole 430 having features 432, 434.
600 Cabinet—preferably, houses power distribution network; refrigerant supply, e.g., RT-4, pump and delivery lines; holds testing device(s) such as of FIGS. 1 and 50, and also serves as mount for instrumentation and displays, and so forth.
610 Test cell device bank site, e.g., site for one device such as generally depicted in FIGS. 1 and 50.
611 Test cell device see-through protective cover, e.g., of ¼-inch thick polymethylmethacrylate.
620 Instrumention, including control, and display.
680 Pulley assembly rail slide.
700 Pulley, string, weight for testing. Compare, ASTM D-4684-98; Selby et al., U.S. Pat. No. 5,852,230.
776 Counting wheel pulley support arm, e.g., of #303/304 stainless steel.
777 Counting wheel pulley, e.g., of DELRIN plastic, or, say, nylon, etc.
778 Counting wheel pulley test string shoulder guide.
779 Counting wheel pulley counting indicia, e.g., printing and/or notches, say, three in number spaced at a 3:1 ratio with respect to the guide 778.
780 Counting wheel pulley base, e.g., of DELRIN plastic, goes over and slidingly engages the rail slide 680.

Any suitable refrigerant may be employed. Accordingly, halocarbons to include chlorofluorocarbons, hydrohalocarbons, halocarbons, or other suitable substances may be employed as a refrigerant under suitable pressures. For an example, the refrigerant can be the well known R507 or AZ-50 refrigerant(s). Two to twelve, or more, flowpaths may be in a single block, particularly those having C-2 to C-12 symmetry or better, for example, to C-infinity symmetry, and separate, opposing flowpaths may be employed. With the opposing flowpaths, two, four, six, or more paths may be in a single block, and three or another odd number of flowpaths may also be employed, say, in a triangular, round, or other correspondingly shaped block. The block may be any suitable shape, including triangular, square, rectangular, pentagonal, hexagonal, hemispherical, spherical, and so forth. With two flowpaths in a rectangularly shaped copper block, and with the cylindrical block with annular copper test well member in a TP-1 type device, 0.2-degree-C control, or 0.1-degree-C control, or even better control, can or may be achieved, in satisfaction or betterment of the parameters of ASTM D-4684. Overall block-temperature can be highly uniform, especially with a radially symmetrical block such as annular or circular blocks.

In opposing flowpath devices, indirect cooling as by a cooled glycol, methanol, etc., may be employed. Direct refrigeration, however, is preferred, to include in devices having one- and multi-flowpath heat-conductable solid member(s) or block(s).

Noting the presence of any heating elements, too, the device may be employed to heat an array of test samples, or one test sample, say, above ambient room temperature. Great control of the temperature in such a system can be achieved.

Calibration of the device can be achieved by known methods.

The Selby et al. patent is incorporated herein by reference.

Thus, it can be understood by those skilled in th art that a direct refrigeration device has a heat-conductable solid member, with a refrigerant passageway from one part to another or on a surface whereof, in which passageway courses a refrigerant which cools primarily by evaporation of the refrigerant from a liquid to a gaseous state inside the passageway, and thermal conduction through the solid member and that an opposing flowpath refrigeration device has at least two passageways which oppose one another in direction of flow of refrigerant with the refrigerant in one passageway flowing in a first direction and the refrigerant in the other passageway flowing in a second direction opposing the first, whether or not cooling in any of the pathways is direct, as noted above, or even indirect, such an by an intermediate coolant that does not provide cooling directly as by evaporation in the heat-conductable solid member but indirectly by being cooled outside and away from the member and, while still cool, being run through the member. And so, it can be appreciated by those skilled in the art that the provisions hereof can generally include the following items:

A. A direct and/or opposing flowpath refrigeration device.

B. The device of item A, which employs direct refrigeration.

C. The device of item A, wherein a test bank is generally annular or cylindrical.

D. The device of item A, which is a fluid testing device having multiple test cello positioned in a block which is cooled to below room temperature for testing.

E. Th device of item B, which is a fluid testing device having multiple test cells positioned in a block which is cooled to below room temperature for testing.

F. The device of item C, which is a fluid testing device having multiple test cells positioned in a block which is cooled to below room temperature for testing.

G. The device of item F, which contains a heating element.

H. The device of item A, which is a directly cooled electronic component.

I. The device of item A, which is a directly cooled mechanical bearing.

J. The device of item A, which is a directly cooled superconducter material.

K. A viscometric and/or rheological test unit embracing a direct and/or opposing flowpath refrigeration device with refrigeration provided by a liquid to gas system, which includes a heat-conductable solid member at a test bank that can accommodate at least one sample call; and a dynamic temperature control system including at least one heater and at least one temperature sensor in said member.

L. The unit of item K, wherein at least one sample cell is present in said bank.

M. The unit of item L, wherein at least one rotor is present in said bank corresponding to the at least one sample cell.

N. The unit of item M, wherein the at least one sample cell includes a radially endowed call bottom pin, and the at least one rot r includes a bottom cup corresponding to the pin.

O. The unit of item N, wherein a dry gas delivery system is present.

P. The unit of item N, wherein a one-piece key system is employed to control starting and stopping of the rotor.

Q. The unit of item N, wherein a two-piece key system la employed to control starting and stopping of the rotor.

R. The unit of item K, wherein a radially symmetrical type of heat-conductable solid member is present.

S. A direct and/or opposing flowpath refrigeration device having a test bank that is a generally rectangular box.

CONCLUSION TO THE INVENTION

The present invention is thus provided. Various features, parts, subsystems, systems, subcombinations, and combinations can be practiced with or without reference to other features, parts, subsystems, systems, subcombinations or combinations in the practice of the invention, and numerous adaptations can be effected within its spirit, the literal claim scope of which is particularly pointed out as follows:

We claim:

1. A direct and/or opposing flowpath refrigeration device comprising a heat-conductable solid member, with at least one refrigerant passageway therethrough or thereabout, which is such that it can be cooled by at least one of direct refrigeration and opposing flowpath refrigeration, wherein;

with direct refrigeration, in at least one of said at least one passageway can course a refrigerant which cools primarily by evaporation of the refrigerant from a liquid to a gaseous state inside the passageway, and thermal conduction through the solid member; provided that, if the device is a rotational viscometric or rheologic test device, it is part of an instrumental system for low temperature viscometric testing of engine oils and so forth in which a bladeless rotor is employed; and with opposing flowpath refrigeration, at least two of the refrigerant passageways are present, and flow of refrigerant in the at least two passageways oppose one another in direction of flow of refrigerant, with the refrigerant in one passageway flowing in a first direction and the refrigerant in the other passageway flowing in a second direction opposing the first direction, whether direct or indirect cooling is employed in either passageway.

2. The device of claim 1, which employs the direct refrigeration.

3. The device of claim 1, which is said instrumental system part, wherein the solid member is in a form of a test bank which is generally annular or cylindrical.

4. The device of claim 1, which, by the direct refrigeration, is a directly cooled electronic component.

5. The device of claim 1, which, by the direct refrigeration, is a directly cooled mechanical bearing.

6. The device of claim 1, which, by the direct refrigeration, is a directly cooled superconducter material.

7. A viscometric and/or rheological test unit comprising a direct and/or opposing flowpath refrigeration device with refrigeration provided by a liquid to gas, direct refrigeration system, which includes a heat-conductable solid member as a test bank that can accommodate a plurality of sample calls, through or about which member is at least one refrigerant pathway for coursing of refrigerant; and a dynamic temperature control system including at least one heater and at least one temperature sensor in said member.

8. The unit of claim 7, wherein a plurality of sample cells is present in said bank.

9. The unit of claim 8, wherein a plurality of rotors is present in said bank corresponding to the plurality of sample cells.

10. The unit of claim 7, wherein a rectangular box type of heat-conductable solid member is present.

11. A direct and/or opposing flowpath refrigeration device comprising a heat-conductable solid member, with at least one refrigerant passageway therethrough or thereabout, which is such that it can be cooled by at least one of direct refrigeration and opposing flowpath refrigeration, wherein:

with direct refrigeration, in at least one of said at least one passageway can course a refrigerant which cools primarily by evaporation of the refrigerant from a liquid to a gaseous state inside the passageway, and thermal conduction through the solid member;

with opposing flowpath refrigeration, at least two of the refrigerant passageways are present, and flow of refrigerant in the at least two passageways oppose one another indirection of flow of refrigerant, with the refrigerant in one passageway flowing in a first direction and the refrigerant in the other passageway flowing in a second direction opposing the first direction, whether direct or indirect cooling is employed in either passageways; and the device is a fluid testing device having multiple test cells positioned in said member, which is a block which is cooled to below room temperature for testing.

12. The device of claim 11, which employs the direct refrigeration.

13. The device of claim 11, wherein the block is in a form of a test bank which is generally annular or cylindrical.

14. The device of claim 11, wherein the block is in a form of a test bank which is a generally rectangular box.

15. The device of claim 11, which contains a heating element.

16. The device of claim 11, wherein a dry gas delivery system is present; and a one-piece or a two-piece key system is employed to control starting and stopping of the rotor.

17. A viscometric and/or rheological test unit comprising a direct and/or opposing flowpath refrigeration device with refrigeration provided by a liquid to gas system, which includes a heat-conductable solid member as a test bank that can accommodate at least one sample cell; and a dynamic temperature control system including at least one heater and at least one temperature sensor in said member, wherein:

with direct refrigeration, in at least one of said at least one passageway can course a refrigerant which cools primarily by evaporation of the refrigerant from a liquid to a gaseous state inside the passageway, and thermal conduction through said member;

with opposing flowpath refrigeration, at least two of the refrigerant passageways are present, and flow of refrigerant in the at least two passageways oppose one another in direction of flow of refrigerant, with the refrigerant in one passageway flowing in a first direction and the refrigerant in the other passageway flowing in a second direction opposing the first direction, whether direct or indirect cooling is employed in either passageway;

at least one sample cell is present in said bank;

at least one rotor is present in said bank corresponding to the least one sample cell; and the at least one sample cell includes a radially endowed cell bottom pin, and the at least one rotor includes a bottom cup corresponding to the pin.

18. The unit of claim 17, wherein a dry gas delivery system is present.

19. The unit of claim 17, wherein a one-piece key system is employed to control starting and stopping of the rotor.

20. The unit of claim 17, wherein a two-piece key system is employed to control starting and stopping of the rotor.

21. A rotor-stator arrangement comprising a sample cell having a radially endowed cell bottom pin, and a rotor having a bottom cup corresponding to the pin.

22. The arrangement of claim 21, further comprising a viscometric and/or rheological test unit in which a plurality of sample cells with pins, and corresponding rotors is present.

23. The arrangement of claim 21, wherein said pin has a radius and said cup has a radius, the ratio of the radius of said pin to said cup being about 31:39.

24. The arrangement of claim 21, wherein said pin has a carbide radius tip.

25. The arrangement of claim 21, wherein the rotor has a heat transmission restriction neck.

26. In a viscometric and/or rheological test unit for testing an oleaginous substance, having a block with at least one test sample well therein, the improvement which comprises an insertable and removable test sample cell sleeve that fits in said well.

27. The improvement of claim 26, wherein said sleeve is in a general form of a cylinder having an open top and a closed bottom and includes at least one of a flat portion to an outside wall surface that extends parallel to a cylindrical axis;

a J-slot opening by the open top of said sleeve for easy removal of the sleeve; and a radially endowed cell bottom pin.

28. A removable test sample sleeve for a rotor-stator arrangement for a viscometric and/or rheological test unit for testing an oleaginous substance, comprising a cylinder having an open top and a closed bottom, and a radially endowed cell bottom pin.

29. The sleeve of claim 28, further comprising a flat portion to an outside wall surface of the cylinder that extends parallel to a cylindrical axis; and a J-slot opening by the open top of said sleeve for easy removal of the sleeve.

30. A stop key for a rotor for a viscometric and/or rheological test unit for testing an oleaginous substance, comprising a generally cylindrical shaft having top and bottom ends and a cylindrical axis; a first substantially flat face about the bottom end of the shaft for engaging a test rotor stop arm of the rotor and thus stopping the rotor from rotating, substantially parallel to if not intersecting with the axis, which faces in a first direction; and a second substantially flat face above the first face substantially parallel to if not intersecting with the axis, and which faces in a direction substantially normal to the first direction of the first face.

31. The stop key of claim 30, which is of one piece.

32. The stop key of claim 30, which is of more than one piece.

33. The stop key of claim 32, wherein the generally cylindrical shaft forms a main stop key piece; the second face extends to the top end and forms an inner flat face; a face mate piece with a flat face is present and mates with the main piece through its face and the inner flat face; two main piece side cut out faces are provided between the top and bottom ends, each substantially planarly perpendicular to the inner flat face; and a mating cap hold is present to hold the main and face mate pieces together.

* * * * *